(12) United States Patent
Goertz et al.

(10) Patent No.: US 9,603,321 B2
(45) Date of Patent: Mar. 28, 2017

(54) **PLANTS WITH INCREASED RESISTANCE TO *DIABROTICA VIRGIFERA* AND *OSTRINIA NUBILALIS***

(75) Inventors: Peter Goertz, Lichtenau (DE); John A. Mihm, Lamberton, MN (US)

(73) Assignee: Agrigentics, Inc., Indianapolis, IN (US)

( * ) Notice: Subject to any disclaimer, the term of this patent is extended or adjusted under 35 U.S.C. 154(b) by 1406 days.

(21) Appl. No.: 12/674,162

(22) PCT Filed: Aug. 22, 2008

(86) PCT No.: PCT/EP2008/061034
§ 371 (c)(1),
(2), (4) Date: May 15, 2012

(87) PCT Pub. No.: WO2009/027347
PCT Pub. Date: Mar. 5, 2009

(65) Prior Publication Data
US 2012/0222173 A1    Aug. 30, 2012

(30) Foreign Application Priority Data

Aug. 24, 2007 (EP) .................................... 07114943

(51) Int. Cl.
*A01H 5/10* (2006.01)
*C12Q 1/68* (2006.01)

(52) U.S. Cl.
CPC ............. *A01H 5/10* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

PUBLICATIONS

Wilson et al. (Journal of the Kansas Entomological Society, 68(3), 1995, pp. 326-331).*
Albrecht et al. (Crop Science, vol. 27 No. 3, abstract only 1 page).*
Michelmore et al. (Proc. Natl. Acad. Sci. USA. vol. 88, pp. 9828-9832. (1991)).*
Abel et al. (Journal of Economic Entomology, vol. 93, No. 3, (2000), pp. 982-988).*
Collard et al. (Euphytica, (2005), 142: pp. 169-196).*

* cited by examiner

*Primary Examiner* — David T Fox
*Assistant Examiner* — Jared Shapiro
(74) *Attorney, Agent, or Firm* — Eric J. Kraus; Barnes & Thornburg LLP

(57) ABSTRACT

The present invention relates to new *Zea mays* plants which are resistant to both Western Corn Rootworm (WCR) and European Corn Borer (ECB) and do not express an insecticidal protein derived from *Bacillus thuringiensis*. The invention is also directed to hybrids, progeny and seeds of those plants.

13 Claims, 14 Drawing Sheets

PLANTS WITH INCREASED RESISTANCE TO *DIABROTICA VIRGIFERA* AND *OSTRINIA NUBILALIS*

SUMMARY

The present invention relates to new *Zea mays* plants which are resistant to both Western Corn Rootworm (WCR) and European Corn Borer (ECB) and do not express an insecticidal protein derived from *Bacillus thuringiensis*. The invention is also directed to hybrids, progeny and seeds of those plants.

BACKGROUND ART

Today, the diversity of plant life is under threat as never before. In agriculture, the widespread adoption of a few improved varieties has narrowed the genetic base of important food crops and led to the disappearance of hundreds of landraces. Using plant genetic diversity is vital to meet future development needs. The present approach is to increase biodiversity in maize WCR and ECB resistance performance. Improving the natural host plant resistance of maize could provide an economical and ecological tool for an integrated pest management (IPM) for Europe.

Field corn (maize) is one of the most important economic and ecological crops over the whole world. Numerous possibilities for its use as animal feed, human consumption and industrial resource have made its cultivation indispensable. Since the 1990s the high yielding performance of maize is threatened through the increasing implication of the Western Corn Rootworm (WCR, *Diabrotica virgifera virgifera* LeConte) and the European corn borer (ECB, *Ostrinia nubilalis* Hübner). Both pests severely affect commercial maize production by decreasing yield stability and, in addition, damaged plants often show an increased susceptibility to secondary infections caused by *Fusarium* spp.

In the EU maize accounts for 8.6 million hectars of production for grain with a value of about 10 billion €/year. 72% of the European maize harvest is used as animal feed (for cattle, swine, poultry) while the remainder is used for human consumption (oil, starch, flour). Corn acreage and yields increased dramatically in France, Italy, Spain and Germany in recent decades as growers abandoned traditional rotations with cereals. As a result, corn has become the only cultivated crop in large areas being grown continuously on the same land year after year. In France, 50% of corn is grown continuously.

About 25% of corn acreage in Spain is in high corn borer pressure areas while 40% is in medium pressure areas. In Germany approximately 25% of the maize acreage is infested with ECB. In France approximately 40% of maize acreage have an average of one or more ECB per corn plant. In Italy, corn borers infest nearly all of the maize acreage every year resulting in yield losses of 7 to 15%. It is estimated that 5 to 7% of potential European corn production (=ca. 260 million €) is lost annually due to borers depending on the intensity of the infestation. Each year only in France, Germany, Spain and Italy 15 million € cost for treatment (insecticide and trichogramma applications) arise (Gianessi et al., 2003).

Preliminary studies on the potential of establishment have shown that WCR is likely to survive and develop wherever maize is grown in Europe. Three to five years after first observation of beetles the pest will have multiplied so that significant yield losses occur. WCR was rated as an EU quarantine pest obliging all European member countries to carry out immediate measures to stop further spread of the pest. Experts predict that the natural spread of WCR in Europe cannot be stopped and further spread of the pest possibly will increase damage costs comparable to those in the US. The most efficient measure against WCR is right now crop rotation, which is not applicable for areas with high percentage of maize in rotation. The high damage costs of already 300 million € in Europe and the situation in the US (ca. 1 billion $ damage and application cost) clearly demonstrate the economic importance of the present invention.

Western corn root worm (WCR, *Diabrotica virgifera virgifera* LeConte) is a North American beetle whose original distribution appears to have been within the foothills to the east of the Rocky Mountains (Colorado, USA). It was first recorded as a pest of maize in 1909 in Colorado. It then slowly spread eastwards to Nebraska (1929), Kansas (1945), Missouri (1960) and Illinois (1964). Continuously grown maize, i.e. without rotation, has largely been responsible for the spread of WCR in North America (Metcalf & Metcalf, 1993). It is now found from Ontario to North Carolina and is present throughout the central and eastern USA and is spreading in Canada (Ontario and Quebec (Meloche et al., 2001)). The rate of spread of WCR in the USA was between 44 and 125 km/year (Onstad et al., 2003).

In Europe WCR was first observed in the vicinity of Surcin airport, near Belgrade (Yugoslavia), on a small maize plot (0.5 ha) in July 1992. It is thought that it may have been introduced in 1990 by military air transport from North America (EPPO, 1996). Nowadays it is obvious that the WCR has spread from its initial infestation point in 1992 to a range of several hundreds of kilometers, affecting many countries in the region. For example, WCR was for the first time found in Italy in 1998 and in France in 2002. All European countries and regions with suitable climatic conditions for maize production are likely to be infested in the next years. In July 2007, for the first time WCR was observed in the Southern part of Germany (http://www.bio-sicherheit.de/de/mais/maiswurzelbohrer/330.doku.html).

The WCR significantly impacts maize production, farmer's income, development of rural communities and poses risk of environmental load through pesticide application. Also, WCR as quarantine pest affects trade of maize in Europe.

Short distance movement of the WCR occurs when the adults of the rootworm walk or fly at low elevations (<5 m above ground level) within and between fields. Such types of movement are responsible for low rates of spread. Greater spread occurs when newly mated females disperse aerially above 10 m at a mean of around 40 km per year.

Larval root feeding is the primary source of damage, reducing nutrient uptake and growth (Gavloski et al., 1992). Larvae cannot discriminate between the roots of plant species (Krysan & Miller, 1986) and will feed on roots closest to where they hatch. Root damage also weakens plants and makes them more susceptible to lodging in wet or windy conditions. This can inhibit or even prevent crop harvesting. Adults feed on flowering maize pollen, silks, leaves and young developing kernels but also on pollen from a wide range of alternate hosts including Asteraceae, Fabaceae, Chenopodiaceae, Poaceae, Solanaceae and Cucurbitaceae.

In Hungary the larval damage threshold is reported to be 20-30 larvae per plant. Even in crops treated with insecticides such as terbufos, damage occurred with 7.5% of the crop lodging. When considering grain yield, adults feeding on kernels at densities of up to 20 adults per ear do not cause significant yield reduction, and moderate levels of silk clipping can be tolerated (Capinera et al., 1986). However, it is the feeding damage to roots by larvae that is most significant.

The insecticide Dursban WG (Chlorpyriphos 75%) has been shown to provide good results against WCR adults, both in US and European trials. For control purposes, it is recommended that Dursban WG is applied every 4 weeks until October. Therefore special spraying machinery may be required in a relatively tall maize crop, late in the season. This was a key limitation in the control program used near Paris, and could also decrease gross margins by raising variable costs.

Trials on insecticide efficacy of soil treatments applied before sowing, at sowing or during the growing season, have been carried out in Serbia. It was concluded that best results were obtained before sowing with terbufos, lindane and bifenthrin; at sowing with terbufos, chlormephos, lindane and bifenthrin; and during the growing season with carbosulfan, terbufos and phorate. In other words, terbufos remains effective throughout. The best protection is obtained with a treatment at sowing (EPPO, 1996), and, ideally, a soil insecticide should persist for 6-10 weeks (Levine & Oloumi-Sadeghi, 1991). Available seed treatments may lack adequate persistence, e.g. the efficacy of "Gaucho" seed treatment or "Cruiser" (thiamethoxam) may be three weeks from planting.

The growing of continuous maize in North America and the regular use of insecticides to control WCR led to resistance to chlorinated hydrocarbons developing in the late 1950's (Metcalf, 1976), and to other insecticides, including carbamates and organophosphates (OPs), more recently. The problem of insecticide-resistant corn rootworm remains, and field trials are carried out each year in the USA to evaluate the effectiveness of alternative soil insecticides for WCR control. In addition, management strategies now emphasize a more IPM-based approach, i.e. utilizing rotation, scouting to determine the need for control, etc.

Among the insect pests that cause damage to corn, two species of corn borers are of particular importance in Europe: European corn borer (ECB, *Ostrinia nubilalis* Hübner) and Mediterranean corn borer (MCB, *Sesamia nonagrioides* Lefèbvre). The ECB is a native of Europe and the major pest in France, Germany, Italy and Spain.

The European corn borer significantly affects production of maize in central Europe. Its distribution in Germany has, in recent years, extended with up to 10 km per year northwards into the cooler climatic regions (Langenbruch and Scewczyk, 1995).

In Central Europe the ECB completes normally one generation (univoltine) per year. In warmer regions, ECB occurs with two or more generations (multivoltine), depending on the geographic latitude and regional climatic conditions. Adults of ECB appear at the end of June and deposit their eggs on plants at the late whorl stage, shortly before anthesis. First- and second-instar larvae feed on leaves and pollen before entering the stalks. Tunneling of the larvae in the stalk and ear shank causes yield losses owing to growth reductions and harvest losses from dropped ears. Secondary infections with pathogens provoke stalk rot and lodging (Jarvis et al. 1984) obstructing mechanical harvest. In addition, the higher incidence of fungal diseases, especially *Fusarium* spp., reduces the forage quality through mycotoxin contamination (Lew et al. 1991). Research has shown that in Europe corn yields are reduced 6% for one ECB larvae per plant.

ECB larvae cause yield losses of up to 30% in regions with a high natural occurrence of ECB due to feeding and tunneling in plants resulting in poor ear development, broken stalks, and dropped ears. Most yield loss can be attributed to the impaired ability of plants to produce normal amounts of grain due to the physiological effect of larval feeding damage in leaf and conductive tissues. With persistent autumn winds and dry weather, tunneling in the stalks and ear shanks can increase stalk and shank breakage, resulting in substantial loss of ears during harvest. Corn hybrids with more rigid stalks and larger shanks will reduce ear loss. Furthermore it is assumed that ECB damage favors secondary mold infections such as *Fusarium* spp. or *Ustilago maydis*, which may lead to additional yield losses and adversely affect the quality of grains. This increase in stalk rot is directly related to ECB larvae boring into stalks and ear shanks. Losses due to weakening of the stalk from tunneling and stalk rot increase when corn harvest is delayed. Early harvest will reduce losses caused by stalk rot and the ECB.

In many maize growing areas, ECB populations exceed the economic threshold and, therefore, farmers are forced to take control measures (Rost 1996). The traditional ECB management method is to destroy shelter for overwintering by crushing maize residues and ploughing. Furthermore, various insecticides (pyrethroid or organophosphate insecticides) as well as bacterial (*Bacillus thuringiensis*, Bt) and biological (*Trichogramma* parasites) control methods for ECB are available. However, ECB larvae on maize plants are difficult to combat, because they are exposed to sprays or antagonists for only a short period of time before they bore into the plant, and therefore efficiency of treatments is limited.

Many corn hybrids have some natural resistance to corn borer feeding. Prior to 1996, all Ontario corn hybrids promoted as "corn borer resistant" were of this type. They are attacked by corn borers but do not suffer much yield loss. The search for germplasm resistant to ECB is therefore essential for successful breeding in Europe. The host plant resistance of maize against the second ECB generation is quantitatively inherited and associated with at least seven genomic regions (Jennings et al. 1974). Bohn et al. (2001) found six quantitative trait loci (QTL) for tunnel length and five QTL for stalk damage rating, explaining about 50% of the genotypic variance in the early maturing European maize germplasm. Furthermore, diallel studies and generation mean analyses confirmed a mainly additive gene action and to a lesser extend dominance and epistatic interactions (Jennings et al. 1974). Molecular markers for marker assisted selection are not available.

Antibiosis based on the concentration of the secondary metabolite hydroxamic acid 2,4-dihydroxy-7-methoxy-1,4-benzoxazin-3-one (DIMBOA) which belongs to the class of benzoxazinoids is reported to provide resistance to some insects and fungal diseases in maize and other cereals (Niemeyer et al, 1995; Hansen L. M., 2004). Therefore it represents an important part of general natural plant defence. Antibiosis to the first ECB generation (leaf feeding resistance) is mainly based on the concentration of the secondary metabolite DIMBOA [2,4-dihydroxy-7-methoxy-(2H)-1,4-benzoxazin-3(4H)-one] in the leaves (Magg, 2004). In addition, antibiosis to the second ECB generation depends on a number of factors such as the concentration of detergent fiber, cellulose, lignin, and biogenic silica in cell walls and tissue toughness.

Seed companies are now marketing Bt corn, one of the first tangible fruits of biotechnology that has practical implications for U.S. and Canadian corn farmers. Bt corn hybrids produce an insecticidal toxin specific to certain insects (e.g.

moths, beetles, blackflies or mosquitoes) derived from the bacterium *Bacillus thuringiensis*, a naturally-occurring soil bacterium that occurs worldwide. These hybrids provide protection against the WCR and ECB equal to, and usually far greater than, optimally timed insecticides. Transgenic maize to produce insecticidal proteins against ECB and WCR have been released to farmers in the USA and for ECB in Europe (ca. 50000 ha Spain).

However, vertical resistance based on a single gene exerts strong selection pressure on the insect population. In general, vertical resistance is controlled by one (or sometimes a few) major resistance (R) genes, each of which corresponds to a parasitic matching gene. The plants are highly resistant to one or several pathogen races, but susceptible to others. Because of the strong selection pressure on the insect population, biotypes resistant to BT may develop fairly rapidly. Magg et al. (2001) observed 0.08 to 0.19 surviving larvae per plant and a percentage of damaged stalks ranging from 18 to 31% for plots planted with Bt hybrids. The authors conclude in case the resistance breaks down, non-transgenic host plant resistance could act as a second barrier for the target pest.

In non-adapted US material broad biotype-nonspecific horizontal resistant donor material was identified in a long-term host plant resistance program. This donor material which is non-adapted for European conditions was evaluated for resistance on several locations in Europe under high pest pressure (WCR in Hungary and ECB in Germany). The inventors are now able to provide several inbred lines resistant against WCR and ECB which show high levels of resistance under European conditions.

Therefore the present invention is directed to a *Zea mays* plant which is resistant to both Western Corn Rootworm and European Corn Borer, wherein the plant does not express an insecticidal protein derived from *Bacillus thuringiensis*.

In the context of the present invention, the term "*Zea mays*" comprises the plant species *Zea mays* and especially the subspecies *Zea mays* L. ssp. *mays* including the Amylacea Group, the Everta Group, the Indentata Group, the Indurata Group, and the Saccharata Group. In the present invention, the term "*Zea mays*" is used interchangeably with the terms "maize" or "corn", the latter being the popular name in the United States, Canada, New Zealand and Australia.

A "plant" can be a mature plant or a seedling. "Mature plants" are to be understood as meaning plants at any developmental stage beyond the seedling. "Seedling" is to be understood as meaning a young, immature plant in an early developmental stage.

The term "Western Corn Rootworm" (WCR) in the context of the present invention comprises the species *Diabrotica virgifera*, also called *Diabrotica virgifera virgifera* and *Diabrotica virgifera* (*virgifera*) LeConte.

The term "European Corn Borer" (ECB) in the context of the present invention comprises the species *Ostrinia nubilalis*, also called *Ostrinia nubilalis* Hübner.

The term "resistant" or "resistance" refers to the sum of a plant's mechanisms that interpose barriers to the invasion or multiplication of infectious agents or pathogens, or to damage by their toxic products or any other damaging factors. As a result, the plant excludes or overcomes, completely or to some degree (see below), the harmful effect of the infectious agents, damaging factors, pathogens or toxic products. Usually, resistance is thought to result from a genetic mutation. Resistance detected by searching a plant's genetic characteristics for mutations thought to confer lower susceptibility is called "genotypic resistance". Resistance found by successfully growing cultures of the plant in the presence of a pathogen is called "phenotypic resistance". Once a phenotypic resistance is detected, the plant can further be analyzed or verified by genetic means, and the corresponding genotypic resistance can be detected. In the present case, resistance may for example be mediated by the production of a toxic agent which leads to the death of the larvae or the production of a repellant which inhibits the feeding of the larvae on the roots.

The term "tolerant" or "tolerance", as opposed to the term "resistant" or "resistance", means the capacity of a plant to experience exposure to unfavorable environmental conditions like a potentially harmful pathogen or the damage caused by its toxic product(s) without showing one or more substantial adverse effects, for example without dying or suffering serious injury or crop loss. The tolerance manifests in a mechanism of adjustment or adaptation. This means for example that the plant is infested by a pathogen, but it compensates the infestation and its consequences by an increased growth or metabolism, especially at the site of infestation. A *Zea mays* plant which is tolerant towards WCR and/or ECB and which is infested by the larvae of WCR and/or ECB might for example respond to the root damage with an increased root growth. The number of viable larvae on the roots, however, does not decrease in this case of tolerance, as opposed to the above-described mechanism of resistance. The non-resistant commercially available maize hybrid "Zamora", for example, shows tolerance, but no resistance, to ECB (see http://www.saatenunion.com/index.cfm/nav/375/article/2664/product/ZAMORA.htm 1). Zamora is registered in Spain under the registration number 980481.

In the present case, the resistance to WCR and/or ECB can, for example, be determined by a factor that is called "lodging rating scale". The "lodging" is defined as state of permanent displacement of a stem crop from its upright position. It is the result of the inability of the stems to support the weight of the plant, for example due to larvae infestation on the plant roots. Lodging is usually rated on a scale of 1 to 9. A score of "1" indicates erect plants, a score of "5" indicates plants are leaning at a 45 degree angle in relation to the ground, and a score of "9" indicates plants are laying on the ground. The following table (Table 1) represents the relation between the three parameters "lodging rating scale", "lodging angle [degree]" and "resistance [%]":

| lodging rating scale | lodging angle (degree) | % resistance |
|---|---|---|
| 1 | 0 | 100 |
| 2 | 11.25 | 87.5 |
| 3 | 22.5 | 75 |
| 4 | 33.75 | 62.5 |
| 5 | 45 | 50 |
| 6 | 56.25 | 37.5 |
| 7 | 67.5 | 25 |
| 8 | 78.75 | 12.5 |
| 9 | 90 | 0 |

Of course, any "intermediate" lodging degree or resistance percentage can be calculated according to the above-defined relations. For example, a 95% resistance is represented by a lodging angle of 4.5 degrees, a 90% resistance is represented by a lodging angle of 9 degrees etc.

In order to determine whether a plant is resistant to both WCR and ECB, the plant is cultivated in a first field, area or plot with WCR infestation and in a second field, area or plot with ECB infestation, and the lodging rating is determined for both fields, areas or plots. A possible experimental setup is described in the examples, but variations of the plot dimensions, the number of reproductions etc. can be applied by the skilled person.

Preferably, the WCR/ECB resistance of the *Zea mays* plant according to the invention is at least about 50%, 55%, or 60%, more preferably at least about 62.5%, 65% or 70%, especially preferably at least about 75%, 80% or 85%, particularly preferably at least about 87.5%, 90% or 95%, and most preferably about 100%, as determined by the lodging rating scale.

The plant according to the invention does not express an insecticidal protein derived from *Bacillus thuringiensis*. The term "expression" or "to express" refers to the biosynthesis of a gene product. For example, in the case of a structural gene, expression involves transcription of the structural gene into mRNA and the subsequent translation of mRNA into one or more polypeptides or proteins. Furthermore, the "expression" may include post-transcriptional processes like mRNA splicing and post-translational modifications like glycosylation as well as targeting of an expression product into a cellular compartment or outside of the cell.

As used herein, the term "amino acid sequence" refers to a list of abbreviations, letters, characters or words representing amino acid residues. Amino acids may be referred to herein by either their commonly known three-letter symbols or by the one-letter symbols recommended by the IUPAC-IUB Biochemical Nomenclature Commission. The terms "peptide", "oligopeptide", "polypeptide", "gene product", "expression product" and "protein" are used interchangeably herein to refer to an oligomer or polymer of consecutive amino acid residues.

The term "insecticidal" or "insecticide" refers to a substance that exerts an activity directed against insects in all developmental forms. They include ovicides and larvicides used against the eggs and larvae of insects as well as adulticides used against the adult insect. The insecticidal substance can either be active exclusively against insects or in addition against other animals, plants or pathogens.

One example of the development of a "biological insecticide" is the use of *Bacillus thuringiensis*, a bacterium that affects Lepidoptera (moths and butterflies) and some other insects. *B. thuringiensis* is a Gram-positive, soil dwelling bacterium of the genus *Bacillus*. Upon sporulation, *B. thuringiensis* forms crystals of proteinaceous insecticidal δ-endotoxins (Cry toxins) which are encoded by cry genes. Cry toxins have specific activities against species of the orders Lepidoptera (moths and butterflies), Diptera (flies and mosquitoes) and Coleoptera (beetles). Thus, *B. thuringiensis* serves as a reservoir of Cry toxins and cry genes for the production of biological insecticides and insect-resistant genetically modified crops. One toxin from *Bacillus thuringiensis* (Bt toxin) can be incorporated directly into plants through the use of genetic engineering.

One important disadvantage of the Bt toxin is that insects develop resistance rapidly when Bt toxin is present in whole plant. Another disadvantage is that the expression of the Bt gene can vary. For instance, if the temperature is not ideal, this stress can lower the toxin production and make the plant more susceptible. More importantly, reduced late-season expression of toxin has been documented, possibly resulting from methylation of the promoter. Due to the constant exposure to the toxin an evolutionary selective pressure is created for resistant pests. Already, the Diamondback moth is known to have evolved a resistance to Bt. There is also a hypothetical risk that, for example, transgenic maize will crossbreed with wild grass variants, and that the Bt gene will end up in a natural environment, retaining its toxicity. Finally, reasons for sudden dying of bt cotton plants in the main field is unknown until now to the bt cotton developers across the world.

In a preferred embodiment, the *Zea mays* plant according to the invention does not express an insecticidal protein derived from a bacterium.

A "bacterium" is a prokaryotic unicellular microorganism. Bacteria are typically a few micrometers long (around 0.5 to 5) and have many shapes. Most bacterial species are either spherical, called cocci, or rod-shaped, called bacilli. Some rod-shaped bacteria, called vibrio, are slightly curved or comma-shaped; others, can be spiral-shaped, called spirilla, or tightly coiled, called spirochetes. A small number of species even have tetrahedral or cuboidal shapes. This wide variety of shapes is determined by the bacterial cell wall and cytoskeleton.

Many bacterial species exist simply as single cells, others associate in characteristic patterns: *Neisseria* form diploids (pairs), *Streptococcus* form chains, and *Staphylococcus* group together in "bunch of grapes" clusters. Bacteria can also be elongated to form filaments, for example the Actinobacteria. Filamentous bacteria are often surrounded by a sheath that contains many individual cells; certain types, such as species of the genus *Nocardia*, even form complex, branched filaments, similar in appearance to fungal mycelia.

The bacterial phyla comprise Actinobacteria, Aquificae, Chlamydiae, Bacteroidetes/Chlorobi, Chloroflexi, Chrysiogenetes, Cyanobacteria, Deferribacteres, Deinococcus-Thermus, Dictyoglomi, Fibrobacteres/Acidobacteria, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae and Verrucomicrobia.

In another preferred embodiment, the *Zea mays* plant according to the invention does not express a transgenic insecticidal protein.

The terms "transgene" or "transgenic" (or "recombinant") refer to a polynucleotide manipulated by man or a copy or complement of a polynucleotide manipulated by man. For instance, a transgenic expression cassette comprising a promoter operably linked to a second polynucleotide may include a promoter that is heterologous to the second polynucleotide as the result of manipulation by man (e.g., by methods described in Sambrook et al., Molecular Cloning—A Laboratory Manual, Cold Spring Harbor Laboratory, Cold Spring Harbor, N.Y., (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, restriction sites or plasmid vector sequences manipulated by man may flank or separate the promoter from the second polynucleotide. One of skill will recognize that polynucleotides can be manipulated in many ways and are not limited to the examples as described herein.

The term "transgenic" or "recombinant" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods well-known to the skilled person. The term "transgenic" or "recombinant" when used in reference to a protein refers to a protein which is encoded by a transgenic polynucleotide.

In another preferred embodiment of the invention, the *Zea mays* plant does not express a transgenic pesticidal protein.

In the scope of the present invention, the term "pesticidal" protein refers to any protein intended for preventing, destroying, repelling, or lessening the damage of any pest. A pesticidal protein may be active against pests including insects, plant pathogens, weeds, molluscs, birds, mammals like rodents, fish, nematodes and microbes (viruses, bacteria, fungi) that compete with humans for food, destroy property, spread or are a vector for disease or are a nuisance. A pesticidal protein or "pesticide" can for example be a bactericide, a fungicide (for the control of fungi and oomycetes), a herbicide (e.g. for the control of weeds), an insecticide (e.g. an ovicide, a larvicide or an adulticide), a miticide, a molluscicide (e.g. for the control of slugs and snails), a nematicide, a rodenticide or a virucide.

A "transgenic pesticidal protein" is a protein as defined above that is encoded by a transgene as defined above and that exhibits a pesticidal action as defined above.

In another preferred embodiment, the *Zea mays* plant according to the invention is at least about 2 times less susceptible to WCR compared to Zamora maize, more preferably at least about 2.5 or 3 times, especially preferably at least about 3.5 or 4 times, particularly preferably at least 4.5 or 5 times and most preferably at least about 5.5 or 6 or 7.5 or 10 times.

Also, in a preferred embodiment, the *Zea mays* plant is at least about 2 times less susceptible to ECB compared to Zamora maize, more preferably at least about 2.5 or 3 times, especially preferably at least about 3.5 or 4 times, particularly preferably at least 4.5 or 5 times and most preferably at least about 5.5 or 6 or 7.5 or 10 times.

The term "susceptible" or "susceptibility" corresponds to the inability of a plant to resist the invasion or multiplication of infectious agents or pathogens, or the damage by their toxic products or any other damaging factors. As a result of susceptibility, the plant is easily affected or sensitive, completely or to some degree, to the harmful effect of the infectious agents, damaging factors, pathogens or toxic products. In other words, an increased susceptibility level corresponds to a reduced resistance level of a plant with respect to a given pathogen or pest, and vice versa, i.e., a reduced susceptibility level corresponds to an increased resistance level.

Another non-resistant commercially available maize hybrid which can be used as a reference plant for the purposes of the present invention is "Astor" which is a non-resistant commercially registered maize hybrid (available from Südwestsaat GbR, Rastatt, Germany, see also the interne page http://www.saaten-union.de or more specifically http://www.saaten-union.de/index.cfm/portal/1/nav/325/article/1726/page/print1.html). Astor is registered in France under the designation "Anjou249" and registration number CTPS 1007587.

Of course, any other non-resistant maize plant can serve as a reference plant for the present invention, such as the non-resistant plants described in the examples.

Other suitable maize lines which can serve as a reference are maize line R 6080 and maize line R 1437, whereby R 6080 is a useful reference with respect to ECB susceptibility and R 1437 with respect to WCR susceptibility. Both lines are available from Südwestsaat GbR (Rastatt, Germany). R 6080 is also registered at the Community Plant Variety Office (grant number R 16016).

In a preferred embodiment, the *Zea mays* plant according to the invention is at least about 2 times less susceptible to WCR compared to maize line R 1437, more preferably at least about 2.5 or 3 times, especially preferably at least about 3.5 or 4 times, particularly preferably at least 4.5 or 5 times and most preferably at least about 5.5 or 6 or 7.5 or 10 times.

Also, in a preferred embodiment, the *Zea mays* plant is at least about 2 times less susceptible to ECB compared to maize line R 6080, more preferably at least about 2.5 or 3 times, especially preferably at least about 3.5 or 4 times, particularly preferably at least 4.5 or 5 times and most preferably at least about 5.5 or 6 or 7.5 or 10 times.

The inventors have also found that the *Zea mays* plant of the present invention is more resistant to WCR than WCR-resistant plants of the prior art, e.g. NGSDCRW1(S2)C4-15-252 (Kahler et al. (1985) Crop Science 25:202) which is called the "gold standard" as all new resistance sources are compared to this standard check inbred line (Bohn (2007) Zeitschrift Mais 34(2): 40-43). The plant of the invention is at least 10%, preferably at least 15%, more preferably at least 20%, even more preferably at least 25% and most preferably at least 30% more resistant to WCR compared to NGSDCRW1(S2)C4-15-252.

One factor that is suitable to determine the resistance of a maize plant to WCR and/or ECB in comparison to a non-resistant reference plant (like "Zamora", "Astor", R 1437 or R 6080) is the number of viable larvae on the roots of the plants, wherein "viable larvae" are those larvae which are able to develop into beetles. In an appropriate experimental setup, the plant according to the invention and the reference plant must be cultivated under identical environmental conditions (location, field size, temperature, humidity, initial pest infestation etc.), most suitably in two neighboring fields. A suitable test arrangement is described in the examples, but possible deviations can also be drawn up by the person skilled in the art.

If a plant is at least about 2 times less susceptible to WCR or ECB compared to a reference plant, there will be at least about 2 times less WCR or ECB larvae, respectively, on the roots. For instance, there might be a number of 30 WCR or ECB larvae on the root of a non-resistant reference plant, and a maximum number of 15 WCR or ECB larvae on the root of a plant according to the invention. Of course, an increased number of maize plants and maize reference plants should be analyzed for statistical reasons, for example 5, 10, 20, 50 or 100 plants.

It is understood that the degree of feeding damage to the roots by larvae is also a suitable indicator of resistance. For scoring the damage caused by WCR larvae, the IOWA scale is commonly used. There are two different scales available, one ranging from 1 to 6 ("old" IOWA scale, Hills and Peters (1971) J. Econ. Entomol. 64(3): 764-765) and one ranging from 1 to 3 ("new" IOWA scale, Oleson et al. (2005) J. Econ. Entomol. 98(1): 1-8) which are both suitable for analyzing the plants of the present invention. Preferably the "new" IOWA scale is used, as the relationship between the numerical scale and the amount of root injury is linear and allows a better distinction between resistant and susceptible plants.

For determining the damage to the root system according to the IOWA scale, plants are grown in regions where the WCR appears frequently since many years. The root system of the *Zea mays* plant is dug out and as much soil as possible is removed from the roots. After washing the roots so that all crown roots are fairly clean, the damage is scored, wherein a value of 0 according to the new IOWA scale means that no visible damage to the root has occurred or that the root shows only a few scars. A value of 3 on the new IOWA scale means that more than one node of roots is completely destroyed. Further information on the scoring of the damage may be obtained from Oleson et al. (2005) J. Econ. Entomol. 98(1): 1-8 which is herein incorporated by reference.

The IOWA root score of the plants of the present invention is between 0.2 and 1.2, preferably between 0.5 and 1.2, more preferably between 0.7 and 1.2 and most preferably between 0.9 and 1.2.°

Another indicator for WCR resistance is larval recovery which indicates the number of larvae on the roots of plants. The larvae are collected by placing whole root balls in fine mesh polyethylene bags and hanging them over water pans in a greenhouse. The larvae will fall down into the water pans and can be stored in 95% ethanol. The method is also described in Hibbard et al. (2004) J. Econ. Entomol. 97(3): 871-882, which is herein incorporated by reference. Greenhouse larvae might be extracted by using Tullgren funnels which create a temperature gradient of approximately 14° C. in a litter or soil sample, stimulating downward movement of soil arthropods into a collecting vessel.

The larval recovery is reduced compared to a susceptible *Zea Mays* plant such as B37×H84, CRW3(S1)C6 and CRW2 (C5), all of which were developed by Bruce Hibbard, USDA-ARS, 205 Curtis Hall, University of Missouri, Columbia, Mo., USA) by at least 20%, preferably at least 25% or 30%, more preferably 35% or 40%, even more preferably 45% or 50% and most preferably 55% or 60%.

The term "root" refers to the underground organ or component of a plant. A root may have several functions and characteristics: It provides support by anchoring the plant to the soil, it absorbs and conducts water and nutrients such as minerals from the soil, and it may store food and waste products. Besides support and storage, the root may also be capable of mutualistic associations with microorganisms and secondary growth in many cases. Usually the root lacks nodes, shoots and leaves.

In another preferred embodiment, the maize plant of the invention is resistant to the Fall Armyworm and/or to the Black Cutworm, in addition to WCR and ECB.

"Fall Armyworm" (*Spodoptera frugiperda*) can be one of the more difficult insect pests to control in maize. Fall Armyworm causes serious leaf feeding damage as well as direct injury to the ear. While fall armyworms can damage corn plants in nearly all stages of development, it will concentrate on later plantings that have not yet silked. Like European corn borer, fall armyworm is most effectively controlled while the larvae are small. Early detection and proper timing of an insecticide application are critical.

The "Black Cutworm" (*Agrotis ipsilon*) is a widespread species which can be found in many regions. The threat of an infestation appears to be greatest in no-till or weedy corn fields, especially in poorly drained areas. The black cutworm feeds on a wide range of field and garden crops. Corn and tobacco are two of its preferred crops. Other known hosts include asparagus, bean, beet, cabbage, castor bean, cotton, grape, lettuce, peanut, pepper, potato, radish, spinach, squash, strawberry and tomato. Black cutworms are among the most destructive of all cutworms. The larvae sever plants from roots near the soil line; usually no other feeding damage is present. Many larvae move from plant to plant on successive nights, while some stay to feed on the roots and underground stems of cut plants.

In another preferred embodiment, the seeds of the *Zea Mays* plant according to the invention are deposited at the "National Collections of Industrial Food and Marine Bacteria" (NCIMB, Aberdeen, UK) under the Accession Numbers NCIMB 41472, NCIMB 41473 and NCIMB 41474 (date of original deposit: 27 Feb. 2007). The respective line designations are AT 0039, R 4535 and R 7222 (see examples).

The "seed" is an organ that develops after fertilization occurs, i.e. a matured ovule. It consists of an embryo, nutrient material (endosperm), and protective coat.

The present invention is also directed to the hybrids of a *Zea mays* plant according to the invention. The term "hybrid" in the present context means a progeny individual resulting from a cross between two genetically distinct parent plants (differing in one or more genes); especially an offspring produced by breeding plants of different populations, varieties, breeds, species, cultivars, genotypes or genera, but generally not different families. In the present context, a "hybrid" is a progeny resulting from a cross wherein at least one of the parent plants is a *Zea mays* plant according to the invention. Preferably, both of the parent plants are *Zea mays* plants according to the invention, being however genetically distinct, as explained above. For example, the hybrid Sum1351 derives from only one resistant parental plant (R7240×AJ 1494), whereas Sum 1352 derives from two parental plants which are both resistant (R 7222×AJ 1499), see FIG. 6.

In plant breeding, hybrids are commonly produced and selected because they have desirable characteristics not found or inconsistently present in the parent individuals or populations. This rearranging of the genetic material between populations or races is also called hybridization.

Since plants hybridize frequently without much work, they are often created by humans in order to produce improved plants. These improvements can include the production of more or better seeds, fruits or other plant parts for consumption, or to make a plant more winter or heat hardy. Much work is now being done with hybrids to produce more disease resistant plants for both agricultural and horticultural crops. In many groups of plants hybridization has been used to produce larger and more showy flowers and new flower colors. Many plant genera and species have their origins in polyploidism, tetraploids are common in a number of different groups of plants and over time these plants can differentiate into distinct species from the normal diploid line. Tetraploids can develop into a breeding population within the diploid population and when hybrids are formed with the diploid population the resulting offspring tend to be sterile triploids, thus effectively stopping the intermixing of genes between the two groups of plants (unless the diploids, in rare cases, produce unreduced gametes). Many hybrids are created by humans, but natural hybrids occur as well. Plant hybrids, especially, are often stronger than either parent variety, a phenomenon which when present is known as hybrid vigour (heterosis) or heterozygote advantage. Plant breeders make use of a number of techniques to produce hybrids.

The present invention is also directed to the progeny of a *Zea mays* plant according to the invention or to the progeny of a hybrid of a *Zea mays* plant according to the invention. In addition, the present invention is directed to the seeds of a *Zea mays* plant according to the invention, to the seeds of the progeny of a *Zea mays* plant according to the invention as well as to the seeds of a hybrid of a *Zea mays* plant according to the invention.

The term "progeny" (or descendant) in the present context is defined as the product of reproduction, sexual or asexual, or replication. It includes, inter alia, a clone, a fruit, a seedling, selfed progeny and descendants, and any propagule of any of these, such as cuttings, which may be used in reproduction or propagation, sexual or asexual. Also encompassed by the term "progeny" is a plant which is a sexually or asexually propagated offspring, clone or descendant of such a plant, or any part or propagule of said plant, offspring, clone or descendant.

In addition to the "whole" plants or the "mature" plants, the invention also comprises progeny, propagation material (such as leaves, roots, seedlings, fruit, pollen, shoots and the like), parts (organs, shoot vegetative structures—e.g. leaves, stems and tubers—, roots, flowers, cuttings, and floral organs/structures, e.g. bracts, sepals, petals, stamens, carpels, anthers and ovules), tissues (e.g. vascular tissue, ground tissue, and the like), cells (e.g. guard cells, egg cells, trichomes and the like), cell cultures, and harvested material, derived from a plant.

The term "cell" or "plant cell" as used herein refers to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronized or not synchronized. A plant cell within the meaning of this invention may be isolated (e.g., in suspension culture) or comprised in a plant tissue, plant organ or plant at any developmental stage.

The term "tissue" with respect to a plant (or "plant tissue") means arrangement of multiple plant cells including differentiated and undifferentiated tissues of plants. Plant tissues may constitute part of a plant organ (e.g., the epidermis of a plant leaf) but may also constitute tumor tissues (e.g., callus tissue) and various types of cells in culture (e.g., single cells, protoplasts, embryos, calli, protocorm-like bodies, etc.). Plant tissue may be in planta, in organ culture, tissue culture, or cell culture.

The further aim of the present invention consists of the development of adapted resistant material using the doubled haploid technology and the development of respective molecular markers in order to facilitate efficient marker based selection procedures.

For example, by combining different sources of monogenic Bt resistance and quantitatively inherited resistances to ECB, it can be possible to develop hybrids with multiple resistance by pyramiding the underlying genes in one genotype (Magg, 2004). To prevent the breakdown of insect resistance, transgenic maize can only be used as one component in an IPM scheme (Schulz et al., 1997). Therefore an effective resistance management system is essential to prevent resistance of ECB to the Bt toxin.

IPM is a sustainable approach to managing pests by combining biological, cultural, physical, and chemical tools in a way that minimizes economic, health, and environmental risks. Economic risks can be minimized through the utilization of approved pest scouting techniques and by implementation of economic thresholds to make pest management decisions. Health risks can be minimized by following all safety directions provided on pesticide labels. Environmental risks can be minimized by avoiding pesticide usage when possible and by following all environmental or wildlife safety guidelines provided on the pesticide label when pesticides must be used.

Linkage maps of the maize genome providing a high genetic resolution have been constructed. SSRs (simple sequence repeats) being a very useful marker system for gene mapping for several reasons have been assigned to the different chromosomes of maize (Bohn et al. 2001). Mapped markers like easy to handle SSRs can be efficiently used in combination with e.g. Bulked Segregant Analysis (Michelmore et al. 1991) in order to identify single resistance genes (e.g. Werner et al. 2000). And they can be used as anchors for the rapid construction of genetic maps for respective crosses being the basis for a QTL-analysis (e.g. Scheurer et al. 2001).

The objective of genetic mapping is to identify simply inherited markers in close proximity to genetic factors affecting quantitative traits (quantitative trait loci, or QTL, those are regions of DNA associated with a particular trait; they provide allelic variation in many cases by combination of genes). This localization relies on processes that create a statistical association between marker and QTL alleles and processes that selectively reduce that association as a function of the marker distance from the QTL. When using crosses between inbred parents to map QTL, in the F1 hybrid complete association between all marker and QTL alleles that derive from the same parent have been created. Recombination in the meioses that lead to doubled haploid (DH), F2, or recombinant inbred lines reduces the association between a given QTL and markers distant from it.

An alternative approach is "association mapping", taking advantage of events that created association in the relatively distant past. Association-based approaches for the detection of QTLs have been largely and effectively used in human genetics, whereas in most plants (with the exception of trees) segregation-based QTL mapping methods are predominant. But association studies become an increasing importance for the analysis for quantitative traits based on the mapping of linkage disequilibrium (LD) in plant population (Flint-Garcia et al. 2003). While segregation-based approaches directly observe the co-inheritance of marker-loci and target genes in a segregating population, a larger population of individual lines is analyzed in association-based approaches in order to reveal associations between marker patterns and trait expressions.

Non-adapted inbred lines can be used as donor for resistance against WCR and ECB for the development of adapted double haploid populations. Double haploid populations have the advantage that because of their special genetic constitution the power of expected QTL mapping analysis is higher compared to conventionally derived S2 or S3 inbred line populations. Additionally, field resistance screenings are more accurate because of higher heritability of the non-segregating double haploid lines. Damage of WCR can be scored according to the "Iowa scale", which scores damage of roots (Oleson et al. 2005). Evaluation of scores is time consuming and therefore an efficient scoring method can be applied: the NIRS technology, analyses for further resistance factors like digestibility (lignin concentration/composition), application of molecular markers, microsatellites (SSRs), SNPs, STSs and ISSR markers for breeding research purposes, etc.

The present approach serves to:
increase the biodiversity in agriculture by the identification of new insect resistance genes,
improve natural host plant resistance as an economically and ecologically promising means to control WCR and ECB infestation,
develop adapted resistant elite inbred lines which can be used to analyze and understand the resistance mechanism against WCR/ECB for high yielding hybrid development, develop efficient scoring methods for WCR damage,
identify closely linked molecular markers facilitating an efficient combination of resistance to WCR/ECB with superior agronomic performance, and
develop adapted elite inbred lines which can be used as components for high yielding resistant hybrids.

The analysis of the genetics of host plant resistance to WCR and ECB with the doubled haploid technology in combination with marker assisted breeding requires expertise in classical breeding techniques, field testing, the application of molecular plant breeding technologies and efficient screening systems for resistance and susceptibility. The development of DH lines and testing them for WCR/ECB resistance in field trials is further supported by chemical analyses and mapping of virus resistance genes. Locations with high natural ECB pressure allow efficient large scale material screening programs under natural pest pressure. Naturally WCR infested fields are used for screening the non-adapted and the developed adapted elite breeding populations.

Today genetics and mechanisms of WCR resistance are unknown and only limited information for ECB resistance is available. By the present approach a future spread of the WCR and the ECB can be avoided or limited and resistant maize accessions in conjunction with molecular markers can serve as the basis for an efficient breeding of resistant adapted elite breeding populations. Improving the natural host plant resistance of maize has an innovative impact for the whole agricultural community. It provides an economical and ecological tool for an integrated pest management system for Europe with a reduction of the risk of yield losses for European farmers.

Therefore, in one embodiment of the invention *Zea mays* plants are provided which are resistant to both Western Corn Root Worm and European Corn Borer, wherein the resistance against Western Corn Root Worm is determined by means of molecular markers and wherein the plants do not express an insecticidal protein derived from *Bacillus thuringiensis*.

In another embodiment of the invention, *Zea mays* plants are provided which are resistant to both Western Corn Root Worm and European Corn Borer, wherein the resistance against European Corn Borer is determined by means of molecular markers and wherein the plants do not express an insecticidal protein derived from *Bacillus thuringiensis*

In yet another embodiment of the present invention, *Zea mays* plants are provided which are resistant to both Western Corn Root Worm and European Corn Borer, wherein the resistance against both Western Corn Root Worm and European Corn Borer is determined by means of molecular markers and wherein the plants do not express an insecticidal protein derived from *Bacillus thuringiensis*

The skilled person knows that it is possible to combine the use of molecular markers for determining resistance to both Western Corn Root Worm and European Corn Borer with other methods for determining resistance, for example the lodging rating scale described herein.

The approach for the detection of QTLs and the comparison to the segregation-based approach directly observed in a segregating population in order to reveal associations between SSR marker patterns and trait expressions offers a high degree of innovation for the whole agricultural community. Both strategies are performed in parallel to increase the possibility of being successful.

The development of efficient screening methods and tools enables the inventors to develop more efficient and faster resistant hybrids and to supply the market with non-GMO resistant hybrids. Especially in countries with low public acceptance of GMO products host plant resistance helps farmers to secure yields. On the other hand host plant resistance in combination with GMO-resistance helps to reduce the risk of resistance breakdown.

By this approach a future spread of the WCR and the ECB can be avoided and resistant/tolerant maize accessions in conjunction with molecular markers serve as basis for an innovative and efficient breeding of resistant adapted elite breeding populations.

One benefit of the invention is on one hand newly developed and well characterized plant material like adapted WCR and ECB resistant inbred lines and hybrids and on the other hand the knowledge about linked molecular markers which enables to develop efficiently new resistant inbreds and hybrids by marker assisted breeding.

"Molecular markers" within the meaning of the present invention are specific DNA segments whose nucleotide sequence differs between different organisms, e.g. resistant and susceptible plants and may therefore be used to distinguish these organisms.

The adapted resistant elite inbred lines can be used to analyze and understand the resistance mechanism against WCR and ECB for future high yielding hybrid development. Extensive field trials for the evaluation of the pre-screened donor material can be combined with an establishment of an easy to handle scoring system.

Based on the identified non-adapted resistant donor material at least two dihaploid mapping populations can be produced which can be used for the genetic analysis of resistance and the identification of linked molecular marker. In order to identify major resistance genes SSRs are used in combination with bulked segregant analysis.

1. Development of Adapted Elite Breeding Populations Resistant to ECB/WCR

Population 1 (POP1) is induced in an induction isolation in Germany. Induced seeds are shipped to the winter nursery (Chile) for haploid selection and D0 multiplication (chromosome doubling, selfing of successful doubled plants). In the same time period initial crosses of population 2 (POP 2) are performed and consequently induction crosses follow. Generation D1 of POP 1 will be available, and seeds of POP 2 in generation D1 will be ready. The development of efficient screening methods is additionally used for screening of resistance in the adapted and non-adapted elite breeding.

2. Evaluation of Mapping Populations POP1 and POP 2 Under Field Conditions

Inbred lines of mapping POP 1 and POP 2 are evaluated under natural insect pressure in replicated field observations (location=4, replication=3). Therefore WCR infested fields are evaluated for larvae contamination/distribution (egg counts/kg soil) to ensure homogenous insect pressure on investigated material. Damage of WCR is scored according to the "Iowa scale", which scores damage of roots (Oleson et al. 2005). For the evaluation of ECB symptoms fields/environments in areas with high risk of ECB infestation are chosen.

3. Development of Efficient Scoring Methods for WCR Damage

For WCR a scoring method is developed to enable high-throughput scoring of root damage of investigated inbred lines. Up to now roots of damaged plants have to be dug out by hand, which is very labor intensive.

4. Molecular Genetic Characterization of the Mapping Population

Parental components of POP 1 are screened for polymorphic SSR markers. Polymorphic SSRs are used for mapping with the main focus on WCR. Leaf material of the 200 double haploid inbred lines is harvested and DNA is isolated therefrom. Additional further marker screenings are performed with bulks of resistant and susceptible DH lines. A QTL analysis for WCR is calculated using marker results (each 200 polymorphic SSRs) of the 200 DH lines with 2 year trait evaluation results.

Another approach to identify molecular markers is SNP (single nucleotide polymorphism) analysis which is a preferred method of the present invention. An SNP is an exchange of a single DNA base or an insertion/deletion of single bases at a specific position within a genomic region such as a gene. Several individuals in a population may e.g. have the base adenine, while other individuals have the base cytosine at the same position within a gene. These exchanges might be indicative for a phenotypic feature such as disease resistance.

The point mutations may be detected on a DNA chip or microarray, by for example allele specific hybridization or primer extension. These detection methods are based on oligonucleotides which are arranged on the chip in the form of a so-called array, i.e. a predetermined arrangement, in order to detect either via hybridization or via hybridization with subsequent DNA polymerase dependent primer extension of the arranged oligonucleotides. For both techniques, the probe, i.e. the respective oligonucleotide, is arranged and fixed at a specific position on the chip, while the nucleic acid molecules of the sample to be examined are present in the form of a hybridization solution. This solution is brought into contact and incubated with the chip, allowing the DNA molecules of the sample, which are present in the solution, to find their appropriate hybridization partner, i.e. the oligonucleotide probe matching the respective molecule, on the surface of the biochip and to hybridize with it. Another method of SNP detection is a multiplex oligonucleotide ligation/polymerase chain reaction with subsequent capillary electrophoresis as described in the examples of the present application.

Preferably, the *Zea mays* plant of the present invention has at least one SNP which is located on a position selected from 197 cM_IBM_map on chromosome 5; 221 cM_IBM_map on chromosome 2; 1008 cM_IBM_map on chromosome 1; 1015 cM_IBM_map on chromosome 1; 659 cM_IBM_map on chromosome 1; 327 cM_IBM_map on chromosome 1; 383 cM_IBM_map on chromosome 2; 192 cM_IBM_map on chromosome 3; 511 cM_IBM_map on chromosome 3; 105 cM_IBM_map on chromosome 8; 251 cM_IBM_map on chromosome 4; 664 cM_IBM_map on chromosome 5; 258 cM_IBM_map on chromosome 7; 250 cM_IBM_map on chromosome 5; 374 cM_IBM_map on chromosome 6; 302 cM_IBM_map on chromosome 6; 277 cM_IBM_map on chromosome 6; 269 cM_IBM_map on chromosome 8; 86 cM_IBM_map on chromosome 7; 241 cM_IBM_map on chromosome 8; 389 cM_IBM_map on chromosome 8; 461 cM_IBM_map on chromosome 8; 238 cM_IBM_map on chromosome 9; 230 cM_IBM_map on chromosome 9 and 314 cM_IBM_map on chromosome 2.

Preferably, the *Zea mays* plant of the present invention has at least two, three, four or five SNPs, more preferably at least six, seven, eight, nine or ten SNPs, even more preferably at least eleven or twelve SNPs and most preferably at least 13 or 14 SNPs located on positions selected from the positions given above.

The *Zea mays* plant of the present invention may further comprise one or more SNPs which are located on a position selected from 142 cM_cons_map on chromosome 1; 72 cM_cons_map on chromosome 2; 90 cM_cons_map on chromosome 2; 127 cM_cons_map on chromosome 3; 54 cM_cons_map on chromosome 4; 148 cM_cons_map on chromosome 6; 80 cM_cons_map on chromosome 7; 81 cM_cons_map on chromosome 7; 93 cM_cons_map on chromosome 8; 115 cM_cons_map on chromosome 8; 98 cM_cons_map on chromosome 9; 74 cM_cons_map on chromosome 10 and 35 cM_cons_map on chromosome 10.

In one embodiment of the present invention, the *Zea mays* plant has a combination of SNPs which are located on positions 197 cM_IBM_map on chromosome 5; 221 cM_IBM_map on chromosome 2; 1008 cM_IBM_map on chromosome 1; 1015 cM_IBM_map on chromosome 1; 327 cM_IBM_map on chromosome 1; 383 cM_IBM_map on chromosome 2; 251 cM_IBM_map on chromosome 4; 664 cM_IBM_map on chromosome 5; 258 cM_IBM_map on chromosome 7; 302 cM_IBM_map on chromosome 6; 277 cM_IBM_map on chromosome 6; 269 cM_IBM_map on chromosome 8; 238 cM_IBM_map on chromosome 9 and 230 cM_IBM_map on chromosome 9. It may further comprise a combination of SNPs which are located on positions 142 cM_cons_map on chromosome 1; 54 cM_cons_map on chromosome 4; 148 cM_cons_map on chromosome 6; 80 cM_cons_map on chromosome 7 and 74 cM_cons_map on chromosome 10.

In another embodiment of the present invention, the *Zea mays* plant has a combination of SNPs which are located on positions 197 cM_IBM_map on chromosome 5; 659 cM_IBM_map on chromosome 1; 383 cM_IBM_map on chromosome 2; 192 cM_IBM_map on chromosome 3; 511 cM_IBM_map on chromosome 3; 105 cM_IBM_map on chromosome 8; 250 cM_IBM_map on chromosome 5; 374 cM_IBM_map on chromosome 6; 86 cM_IBM_map on chromosome 7; 241 cM_IBM_map on chromosome 8; 389 cM_IBM_map on chromosome 8; 461 cM_IBM_map on chromosome 8 and 314 cM_IBM_map on chromosome 2. It may further comprise a combination of SNPs which are located on positions 72 cM_cons_map on chromosome 2; 90 cM_cons_map on chromosome 2; 127 cM_cons_map on chromosome 3; 81 cM_cons_map on chromosome 7; 93 cM_cons_map on chromosome 8; 115 cM_cons_map on chromosome 8; 98 cM_cons_map on chromosome 9 and 35 cM_cons_map on chromosome 10.

Most preferably, the *Zea mays* plant of the present invention has a combination of SNPs which are located on positions 197 cM_IBM_map on chromosome 5 and 383 cM_IBM_map on chromosome 2.

Preferably, the SNP on position 197 cM_IBM_map on chromosome 5 is a A/T exchange; on position 221 cM_IBM_ map on chromosome 2 is a C/T exchange; on position 1008 cM_IBM_map on chromosome 1 is a A/C exchange; on position 1015 cM_IBM_map on chromosome 1 is a A/T exchange; on position 659 cM_IBM_map on chromosome 1 is a C/T exchange; on position 327 cM_IBM_ map on chromosome 1 is a A/C exchange; on position 383 cM_IBM_map on chromosome 2 is a A/C exchange; on position 192 cM_IBM_map on chromosome 3 is a A/G exchange; on position 511 cM_IBM_map on chromosome 3 is a C/G exchange; on position 105 cM_IBM_map on chromosome 8 is a C/T exchange; on position 251 cM_IBM_ map on chromosome 4 is a G/T exchange; on position 664 cM_IBM_map on chromosome 5 is a A/G exchange; on position 258 cM_IBM_map on chromosome 7 is a C/T exchange; on position 250 cM_IBM_ map on chromosome 5 is a A/G exchange; on position 374 cM_IBM_map on chromosome 6 is a A/G exchange; on position 302 cM_IBM_map on chromosome 6 is a A/G exchange; on position 277 cM_IBM_map on chromosome 6 is a A/G exchange; on position 269 cM_IBM_map on chromosome 8 is a A/T exchange; on position 86 cM_IBM_map on chromosome 7 is a C/G exchange; on position 241 cM_IBM_map on chromosome 8 is a G/T and/or a C/G exchange; on position 389 cM_IBM_map on chromosome 8 is a C/G and/or a C/T exchange; on position 461 cM_IBM_map on chromosome 8 is a A/C exchange; on position 238 cM_IBM_map on chromosome 9 is a A/C exchange; on position 230 cM_IBM_map on chromosome 9 is a C/G exchange and on position 314 cM_IBM_map on chromosome 2 is a A/T exchange.

Preferably, the SNP on position 142 cM_cons_map on chromosome 1 is a G/T exchange; on position 72 cM_cons_map on chromosome 2 is a NT exchange; 90 cM_cons_map on chromosome 2 is a A/G exchange; 127 cM_cons_map on chromosome 3 is a A/G exchange; 54 cM_cons_map on chromosome 4 is a A/C exchange; 148 cM_cons_map on chromosome 6 is a C/T exchange; 80 cM_cons_map on chromosome 7 is a C/G exchange; 81 cM_cons_map on chromosome 7 is a A/G exchange; 93 cM_cons_map on chromosome 8 is a G/T exchange; 115 cM_cons_map on chromosome 8 is a A/G exchange; 98 cM_cons_map on chromosome 9 is a C/T exchange; 74 cM_cons_map on chromosome 10 is a A/C exchange and 35 cM_cons_map on chromosome 10 is a C/T exchange.

The presence of an SNP is detected by comparing the sequence of a specific locus identified by its position on a chromosome of resistant plants and susceptible plants with the sequence of the same locus in the parent plants and determining deviations from the expected allele frequency. A deviation from the expected allele frequency is considered significant if one allele shows at least twice as high frequency compared to the other allele and if the difference between the allele frequency is at least 0.2.

The description of the position of the SNPs of the present invention in cM_IBM_map is based on the IBM2 2005 neighbours map which is available under http://www-.maizegdb.org/map.php#rep and which is also described in Schaeffer et al. (2006) Plant and Animal Genome Conference XIV (P372): 200. The description of the position of the SNPs of the present invention in cM_cons_map is based on a consensus map which was developed by the company Trait Genetics. Further information about the molecular markers used and their position is available from Trait Genetics, Am Schwabeplan 1b, 06466 Gatersleben, Germany. The skilled person knows how to determine the position of the SNP on the basis of this information. The term "cM" as used to describe the genetic locus of the SNPs refers to the unit "centimorgan" which is used in genetics as measure to describe a distance along a chromosome, e.g. the relative distance between two genes on a chromosome. One centimorgan corresponds to 1% chance that a marker at one genetic locus on a chromosome will be separated from a marker at a second locus due to crossing over.

The invention further relates to a method of identifying plants which are resistant to both Western Corn Root Worm and European Corn Borer or which are resistant to Western Corn Root Worm by detecting at least one of the single nucleotide polymorphisms listed above in genetic material isolated from the plants. Preferably, the resistance of the plants having at least one single nucleotide polymorphism is confirmed by a method selected from the group consisting of determining the lodging on a 1-9 lodging rating scale, determining root damage by use of the 0-3 Iowa scale or determining larval recovery. The invention also relates to plants identified by such method.

The following examples are used to illustrate the present invention, but should not be construed as limiting.

EXAMPLES

1. Generation of WCR/ECB Resistant Maize Lines

The breeding method for the resistant lines was the following: The parent material was recombined with the subsequent selfed generations at simultaneous artificial infestation with the larvae of WCR and ECB according to the bazooka technique described in the literature. The parent material of the lines AT0039, R4535, and R7222 (see table below) are genetically broad, but heterotically clearly defined synthetics with a portion of 25% of HPR exotics.

HPR exotics derive from tropical/subtropical genetic material. A HPR donor is a "(natural) host plant resistance" donor which has been bred along with artificial infestation to exhibit stable resistance against a high number of maize pests.

The bazooka technique is a method for the targeted application of a certain amount of larvae on the maize plant. It was developed by Dr. J. A. Mihm in 1979. See also Wiseman, B. R; Widstrom, N. W. Comparison of methods of infesting whorl-stage corn with fall army-worm larvae. Journal of Economical Entomology v. 73, p. 440-442, 1980. The larvae application occurred at the point of time that represents the optimal growth of the maize plant for the larvae to feed, according to the natural relationship between the plant and the insect.

The following Zea mays lines were generated (Table 2):

| Line | genetic origin | parent material | status |
| --- | --- | --- | --- |
| AT0039 | USA BSSS Dent, Exotic | BSSS crossed with HPR donor | resistant |
| AT6004 | USA Lancaster Dent | Lancaster Elite recombination | susceptible |
| R1437 | Europa-FlintxDent | Elite Flint-BSSS Synthetic | susceptible |
| R4535 | USA BSSS Dent, Exotic | BSSS crossed with HPR donor | resistant |
| R5525 | USA Reid Dent, Exotic | Elite Reid-Dent with HPR donor | resistant |
| R6080 | USA/Europe Dent Mix | Recombination of 3 Elite Dentlines | susceptible |
| R6305 | Arg./Europe Cateto/Flint | Recombination of Cateto-Flint Pool | susceptible |
| R7222 | USA/Europe Dent, Exotic | Recombination of USA/Europe Elite Dent with HPR donor | resistant |
| R7226 | USA/Europe Dent, Exotic | Recombination of USA/Europe Elite Dent with HPR donor | resistant |
| AJ1499 | Europe-dent x Exotic | european early dent crossed with HPR donor | tolerant |
| AT3030 | USA/Europe dent | Recombination of USA/Europe elite Dent | resistant |

BSSS is defined as the Iowa Stiff Stalk Synthetic, as described by Hallauer and Miranda (Hallauer, A. R.; Miranda Filho, J. B. Quantitative genetics in maize breeding. 2.ed. Ames: Iowa State University Press, 1988). BSSS is a well-known heterotically important gene pool for the temperate maize cultivation.

2. Selection of the Fields

The test areas were selected in those regions where the pests appear frequently since many years and cause substantial economic losses in normal years. For the selection of the areas, all parameters were considered which support a high infestation pressure, such as: cultivation of maize after maize, no rotating (reversing) soil working or tilling etc. In addition, for the WCR locations, soil samples were taken in winter, in order to select the most infested locations by washing the WCR eggs from the soil or by counting the larvae that hatched in the laboratory.

3. Experimental Setup

The testing of inbred plants was performed in Hungary for WCR, in Germany against ECB and in the USA against WCR and ECB. At the locations in the USA, additional WCR or ECB larvae were applied in order to increase the infestation pressure.

The general test arrangement was a randomized block arrangement. The experiments were performed in two rows at a parcel length of 5 meters and with a three-fold reproduction.

In order to control the stability of the resistance, so-called strip tests at a parcel size of about 80 square meters were performed with selected hybrids with a four-fold reproduction. Four locations were tested in Europe: two locations in Hungary, wherein one site showed heavy WCR infestation, and in the other site there was no visible root damage, but some adult insects were found in traps. Both sites were taken to yield. The other two locations were in Germany, wherein one site showed late/moderate ECB attack, and one site was taken to yield.

4. Test Evaluation for WCR

Since the middle of June, several pheromone traps are installed in every test location and are analyzed for WCR beetles at a three-day-interval. This procedure allows an assessment of the infestation pressure. At the time of bloom, a visual rating is performed with respect to the lodging due to root damage by WCR larvae. Based on these results, some selected plants were dug out for the rating of the roots. This rating is performed according to the IOWA scale which is common in the USA.

The IOWA scale has been established for the assessment of the amount of damage by larval feeding of *D. virgifera virgifera* on maize roots. This assessment can be done by digging out the root system taking a diameter of approximately 25 cm to a depth of 15 cm. As much soil as possible is removed from the roots by gentle shaking and/or beating, care being taken not to break off any of the crown roots. The root systems are then washed so that all crown roots are fairly clean.

Damage on the root systems can be assessed by using a scale such as the following ("destroyed" means "of no functional value to the plant"):

1=No visible damage or only few minor feeding scars;
2=Visible feeding scars present but no roots eaten off to within 4 cm of the plant, or with one or two shortened roots if the rest of the system was relatively free of damage;
3=Several roots eaten off to within 4 cm of the plant, but never the equivalent of an entire node of roots destroyed;
4=One node of roots destroyed or the equivalent completely destroyed;
5=Two nodes of roots destroyed completely;
6=Three or more nodes completely destroyed (not illustrated, but similar to a rating of five).

Shortly before the harvest, another rating is performed with respect to the lodging due to root damage by WCR larvae. A harvest is performed, if necessary.

5. Test Evaluation for ECB

Since the middle of July, the test areas are inspected at regular intervals for ECB infestation. At differentiation of the infestation, ratings are performed. The most important rating is performed shortly before the harvest. A harvest is performed, if necessary.

The following table shows a summary of the results (Table 3):

|  | resistant to | susceptible to | ECB 2005 USA | ECB 2005 EU | ECB 2006 USA | ECB 2006 EU | WCR 2005 USA | WCR 2005 EU | WCR 2006 USA | WCR 2006 EU |
|---|---|---|---|---|---|---|---|---|---|---|
| Line |  |  |  |  |  |  |  |  |  |  |
| R7222 | WCR |  | 2/3 | 3/2 | 4/3 | 8/3 | 2/2 | 2/2 | 5/2 | 12/2 |
| AJ1499 | WCR |  | 2/6 |  |  | 8/6 |  |  |  |  |
| R7226 | ECB |  |  | 3/2 |  | 8/2 |  |  |  |  |
| R5525 | ECB |  | 2/1 |  | 4/2 |  |  |  |  |  |
| AT0039 | WCR/ECB |  | 2/2 | 2/2 | 12/2 | 8/2 | 2/2 | 2/2 | 5/2 | 12/2 |
| R4535 | WCR/ECB |  | 2/2 | 2/2 | 12/2 | 8/2 | 2/1 | 2/2 | 5/2 | 12/2 |
| reference lines: |  |  |  |  |  |  |  |  |  |  |
| R6080 |  | ECB |  | 3/7 |  | 12/7 |  |  |  |  |
| R6305 |  | ECB | 2/6 |  | 9/7 |  |  |  |  |  |
| AT6004 |  | WCR |  |  |  |  | 2/6 |  | 9/7 |  |
| R1437 |  | WCR |  |  |  |  | 2/7 | 3/7 |  |  | n = number of results
ll = level of lodging (scale 1 = highly resistant to 9 = highly susceptible)

6. Evaluation of Pest Pressure on the Different Screening Locations

To evaluate pest pressure on the different screening locations beginning of June 2008 on each location 4 pheromone traps were put up and the amount of beetles caught in the traps was counted regularly and the mean value of the four pheromone traps was calculated. The results of the evaluation on the locations Villany, Szentlörinc and Dalmand are shown in FIG. 9. On all locations natural pest pressure was high ranging from 1374 in Villany to 1876 in Szentlörinc and up to 1896 in Dalmand. Literature reports state economic damage occurs if 0.5 to 1.0 adult beetle is found per plant. Observed beetle numbers indicate high pest pressure or high economic damage on all three screening locations.

7. WCR Resistance of Hybrid Plants

To demonstrate/confirm the western corn root worm resistance of the SWS hybrids an evaluation trial was started with expected susceptible competitor hybrid checks (DKC5143, PR37F73, PR35P12, DK440, PR38R92, DKC3511 and PR36K67) and one SWS susceptible hybrid check (ZAMORA) and 5 experimental hybrids developed with parental components with western corn root worm resistance. Hybrids were planted on three locations (Dalmand, Villany and Szentlörinc), with 4 replications in 3 m plots with in average 20 planted seeds per row. In each replication (=row) 5 single plants were dig and Iowa root scores (0-3) were measured to evaluate root damage caused by western corn root worm larvae.

The following table shows the average root scores of every hybrid obtained on three Hungarian locations (Dalmand, Szentlörinc and Villany) (Table 4):

| Hybrid name | Pedigree | Status | Iowa scale 0-3 |
|---|---|---|---|
| DKC5143 | DKC5143 | Check variety | 1.52 |
| PR37F73 | PR37F73 | Check variety | 1.66 |
| PR35P12 | PR35P12 | Check variety | 1.56 |
| ZAMORA | ZAMORA | Check variety | 1.58 |
| DK440 | DK440 | Check variety | 1.52 |
| PR38R92 | PR38R92 | Check variety | 1.60 |
| DKC3511 | DKC3511 | Check variety | 1.42 |
| PR36K67 | PR36K67 | Check variety | 1.56 |
| SUM2163 | AJ1453/AT3030 | SWS Resistant variety | 1.15 |
| SUM2169 | AT0039/AT3030 | SWS Resistant variety | 1.11 |
| SUM2170 | AJ1472/R6306 | SWS Resistant variety | 1.01 |
| SUM2162 | R7222/R6306 | SWS Resistant variety | 1.16 |
| R6309/AJ1453 | R6309/AJ1453 | SWS Resistant variety | 1.10 |

The heritability is defined as the proportion of genetic variance on phenotypic variance. The operative heritability is calculated by determining the variance components and calculating the heritability by the following formula:

$$h^2 = \frac{vc_G}{vc_G + \frac{vc_{GO}}{N_O} + \frac{vc_{GJ}}{N_J} + \frac{vc_{GOJ}}{N_{(OJ)}} + \frac{vc_{error}}{N_{(OJR)}}}$$

A heritability of 1.0 means that differences in WCR resistance are completely based on genetics, while a value of 0 means that the differences are based completely on the environment.

The operative heritability of the experiment was calculated using Plabstat, a computer software for the evaluation of plant breeding trials using the model:
G=Genotypes
L=Location
R=Replication
Y=G+L+R:L+GL+GR:L The calculated heritabilities were:
Location Dalmand: 0.66
Location Szentlörinc: 0.21
Location Villany: 0.52
All locations: 0.72

Differences between genotypes, locations and replications were all highly significant ($\alpha$=0.01). All tested SWS resistant hybrids showed lower root damage scores compared to all tested susceptible hybrids. The SWS resistant hybrids (1.11) showed in average a 28.4 lower root damage compared to the average of all susceptible hybrids (1.55). The best hybrid SUM2170 with a root score of 1.01 showed a 39.2% lower root damage compared to the most susceptible hybrid PR37F73 (1.66).

8. WCR Resistance of Inbred Lines

To demonstrate/confirm the western corn root worm resistance of the SWS inbred lines an evaluation trial was started with one susceptible check (AC3512) and one commonly known resistance source (NGSDCRW1(S2)C4-15-252) with two SWS inbred lines in 2008.

AC3512 is an elite inbred line of SWS without any genetic background related to western corn root worm resistance (susceptible check). NGSDCRW1(S2)C4-15-252 is a western corn rootworm resistant inbred line which was developed through 4 cycles of recurrent selection out of the synthetic NGSDCRW1(S2)C4. NGSDCRW1(S2)C4-15-252 is called the "gold standard", all new resistance sources are compared to this standard check inbred line (Bohn, M. 2007. Der Maiswurzelbohrer in den USA, Zeitschrift Mais 34, 2: 40-43). R7222 and AT3030 are SWS inbred lines with high western corn root worm resistance.

Therefore on three Hungarian locations (Dalmand, Villany and Szentlörinc) with reliable and homogene natural western corn rootworm pressure 4 inbred lines were planted in 3 m rows with 2 (R7222, AT3030), respectively with 4 replications (AC3512, NGSDCRW(S2)-15-252). In each replication 5 single plants were dig and Iowa root scores (0-3) were measured to evaluate root damage caused by western corn root worm larvae. In total for AC3512 and NGSDCRW1(S2)C4-15-252 60 single plants and for R7222 and AT3030 30 single plants were scored.

The following Table shows the mean root scores on the Iowa scale 0-3 of the 4 inbred lines (Table 5):

| Line | Dalmand | Villany | Szentlörinc | Mean |
|---|---|---|---|---|
| AC3512 | 2.17 | 1.87 | 1.98 | 2.01 |
| NGSDCRW(S2)C4-15-2S2 | 1.02 | 1.24 | 1.76 | 1.34 |
| R7222 | 1.25 | 0.88 | 0.74 | 0.96 |
| AT3030 | 1.25 | 1.03 | 1.19 | 1.15 |

As expected AC3512 was susceptible to western corn root worm (mean score 2.01), while the golden standard NGSDCRW1(S2)C4-15-252 showed at least some tolerance with an average root score of 1.34. Highly resistant inbred line R7222 showed a 52.2% lower average root damage compared to AC3512 and even still 28.4% compared to the golden standard.

9. Mapping of Molecular Markers
a) Trait Evaluation

In 2008 two double haploid populations (H06103=R2721/R7222; H06107=AJ1472/AL0158) were tested in field trials to analyse the genetic mechanism of WCR and ECB resistance. Both populations were crosses between an elite parent without WCR/ECB resistance (R2721; AL0158) and an parent with observed resistance (R7222; AJ1472) to WCR/ECB. Therefore 37 genotypes (DH lines) of population H060107 and 143 genotypes (DH lines) of H060103 and the 4 parents of the two mapping populations were tested on 4 heavily with WCR infested (natural infestation) locations in Hungary (Dalmand, Villany, Szentlörinc, Nagyszenas) and on 2 locations in Germany (Oderbruch, Kraichgau) and 1 in France (Reitwiller) with heavy ECB damage (known from evaluations of former years). On each location 4 replications with each 20 kernels/4 m row were planted in spring 2008. On the WCR locations root lodging and root damage (Iowa scale 0-3) were evaluated. Therefore 5 plants of each row were dig with a shovel and after cleaning with a high pressure cleaner scored visually root by root.

The population averages in the different locations/replications (R1-4) as determined with the Iowa scale (0-3) were (Table 6):

| Population | Location | Mean R1 | Mean R2 | Mean R3 | Mean R4 | Total Mean |
|---|---|---|---|---|---|---|
| H06107 | Dalmand | 1.61 | 1.24 | 2.14 | 1.55 | 1.63 |
|  | Szentlörinc | 1.00 | 1.19 | 1.44 | 1.67 | 1.34 |
|  | Lapancsa | 2.44 | 2.00 | 1.23 | 1.01 | 1.68 |
| H06103 | Dalmand | 1.21 | 1.74 | 1.89 | 1.28 | 1.53 |
|  | Szentlörinc | 1.34 | 1.41 | 1.4 | 1.5 | 1.41 |
|  | Lapancsa | 2.02 | 2.39 | 1.31 | 0.89 | 1.65 |

The distribution of single lines of population H06107 and H06103 on the Iowa scale is shown in FIG. 10.

b) Bulk Segregant Analyses

To identify molecular markers which are associated with ECB/WCR resistance a bulk segregant analyses using SNP markers was conducted. SNPs are the most abundant genomic markers, and SNP genotyping, therefore, is a key technology for genome-wide analysis of genetic variation.

For the molecular marker analyses the SNP analysis platform SNPlex developed by APPLIED BIOSYSTEMS was used. This system uses a multiplex oligonucleotide ligation/polymerase chain reaction and capillary electrophoresis to analyze bi-allelic single nucleotide polymorphism genotypes. It generates 4608 data points from a single 96 well plate. This throughput, along with built-in quality control features, data analysis tools and automated assay design, now allows large scale studies to be carried out at high accuracy within a very short period of time. The SNPlex genotyping system consists of a set of pre-optimized, universal assay reagents that are utilized independently of the specific SNPs studied. The only SNP-specific components of the assay are the ligation probes that participate in the oligonucleotide ligation (OLA). Currently, up to 48 SNPs can be addressed simultaneously in one OLA reaction. The assay workflow for the SNPlex genotyping system involves the following seven steps: (1) allele-specific OLA reaction using allele-specific and locus-specific primers; (2) purification of OLA products by exonucleolytic digestion of excess probes and linkers; (3) universal PCR reaction to amplify ligation products using universal primers; (4) capturing of biotin-labeled PCR products in streptavidin coated microtiter plates; (5) binding of fluorescent zipchute probes to single-strand PCR products; (6) elution of hybridized zipchute probes; and (7) fluorescence detection by capillary electrophoresis in an ABI 3730xl sequencer. Analysis is performed using GeneMapper 4.0 genetic analysis software. GeneMapper uses empirical parameters, such as signal strength and cluster separation, to determine whether the plot characteristics of a SNP are within assay specifications.

In a first approach one 96 well plate was developed with the 4 parents (twice), 6 technical controls and 82 genotypes from both populations. Genotypes were selected using the WCR Iowa scale root scores of the two most informative locations (Dalmand/Szentlörinc). Six different SNPlex assays covering a total of 288 different SNP's were used to determine the marker polymorphisms of the parental components of the two populations and also to evaluate allele frequency differences between susceptible and resistant genotypes. Therefore susceptible and resistant genotypes were bulked. For the resistant bulk only genotypes were used with a mean Iowa root score of <1.2 and as susceptible all genotypes with a root score of >1.5. Genotypes with root scores between 1.2 and 1.5 were classified as tolerant and therefore excluded from the bulk segregant analyses.

Susceptible bulk H06103: 12 Genotypes
Resistant bulk H06103: 26 Genotypes
Susceptible bulk H06107: 6 Genotypes
Resistant bulk H06107: 9 Genotypes On several chromosomes significant deviations from the expected allele frequency were observed (see Table 7). A deviation from the expected allele frequency was stated if one allele showed at least twice as high frequency compared to the other allele and if the difference was at least 0.2.

Major effects were detected on chromosome 1 (6 SNP markers, 86cM-197cM) and 6 (3 SNP markers, 56cM-68cM) for population H06103 according to the consensus map and on chromosome 8 (7 SNP markers, 65cM-115cM) for population H06107 according to the consensus map.

TABLE 7

SNP markers with deviations (indicated with *) from the expected allele frequency for susceptible (S) and resistant (R) bulks of population H06103 and H06107.

| SNP | Xchange | AF H06103-S | AF_H06103_R | AF_H06107_S | AF_H06107_R | Chr TG | cM_cons_map | ChrIBM | cM_IBM_map |
|---|---|---|---|---|---|---|---|---|---|
| SNP 109 | G/T | 0.62* | 0.36* | 0.00 | 0.00 | 1 | 142 |  |  |
| SNP 111 | A/T | 0.23* | 0.75* | 0.11* | 0.50* | 1 | 165 | 5 | 197 |
| SNP 143 | C/T | 0.38* | 0.64* | 1.00 | 1.00 | 1 | 139 | 2 | 221 |
| SNP 152 | A/C | 0.25* | 0.46* | 0.00 | 0.00 | 1 | 197 | 1 | 1008 |
| SNP 163 | A/T | 0.65* | 0.27* | 0.00 | 0.00 | 1 | 180 | 1 | 1015 |
| SNP 183 | C/T | 1.00 | 1.00 | 0.11* | 0.5* | 1 | 134 | 1 | 659 |
| SNP 217 | A/C | 0.46* | 0.75* | 1.00 | 1.00 | 1 | 86 | 1 | 327 |
| SNP 44 | A/T | 1.00 | 1.00 | 0.22* | 0.67* | 2 | 72 |  |  |
| SNP 90 | A/C | 0.38* | 0.64* | 0.33* | 0.67* | 2 | 97 | 2 | 383 |
| SNP 223 | A/G | 1.00 | 0.96 | 0.22* | 0.67* | 2 | 90 |  |  |
| SNP 86 | A/G | 0.96 | 0.91 | 0.00* | 1.00* | 3 | 147 | 3 | 192 |

TABLE 7-continued

SNP markers with deviations (indicated with *) from the expected allele frequency for susceptible (S) and resistant (R) bulks of population H06103 and H06107.

| SNP | AF Xchange | AF_H06103-S | AF_H06103_R | AF_H06107_S | AF_H06107_R | Chr TG | cM_cons_map | ChrIBM | cM_IBM_map |
|---|---|---|---|---|---|---|---|---|---|
| SNP 93 | C/G | 0.98 | 1.00 | 0.22* | 0.50* | 3 | 81 | 3 | 511 |
| SNP 104 | C/T | 0.02 | 0.05 | 0.44* | 0.17* | 3 | 127 | 8 | 105 |
| SNP 160 | A/G | 0.02 | 0.04 | 0.39* | 0.17* | 3 | 127 | | |
| SNP 120 | A/C | 0.42* | 0.73* | 0.00 | 0.00 | 4 | 54 | | |
| SNP 154 | G/T | 0.52* | 0.29* | 0.00 | 0.00 | 4 | 46 | 4 | 251 |
| SNP 72 | A/G | 0.58* | 0.33* | 0.00 | 0.00 | 5 | 130 | 5 | 664 |
| SNP 123 | C/T | 0.42* | 0.64* | 0.00 | 0.00 | 5 | 128 | 7 | 258 |
| SNP 195 | A/G | 0.98 | 0.96 | 0.00* | 0.50* | 5 | 105 | 5 | 250 |
| SNP 122 | C/T | 0.23* | 0.50* | 0.22 | 0.33 | 6 | 148 | | |
| SNP 139 | A/G | 0.98 | 0.95 | 0.33* | 0.17* | 6 | 71 | 6 | 374 |
| SNP 205 | A/G | 0.33* | 0.58* | 0.00 | 0.00 | 6 | 62 | 6 | 302 |
| SNP 242 | A/G | 0.36* | 0.58* | 0.00 | 0.00 | 6 | 56 | 6 | 277 |
| SNP 266 | A/T | 0.70* | 0.50* | 0.22 | 0.17 | 6 | 68 | 8 | 269 |
| SNP 9 | C/G | 0.54* | 0.38* | 0.00 | 0.00 | 7 | 80 | | |
| SNP 170 | C/G | 0.52 | 0.50 | 0.55* | 0.17* | 7 | 115 | 7 | 86 |
| SNP 239 | A/G | 0.00 | 0.00 | 0.44* | 0.83* | 7 | 81 | | |
| SNP 13 | G/T | 1.00 | 0.96 | 0.22* | 0.50* | 8 | 65 | 8 | 241 |
| SNP 29 | C/G | 1.00 | 1.00 | 0.00* | 0.50* | 8 | 93 | 8 | 389 |
| SNP 58 | A/C | 0.02 | 0.08 | 0.11* | 0.50* | 8 | 111 | 8 | 461 |
| SNP 112 | G/T | 0.40 | 0.30 | 1.00* | 0.50* | 8 | 93 | | |
| SNP 213 | C/G | 0.98 | 0.92 | 0.22* | 0.50* | 8 | 65 | 8 | 241 |
| SNP 260 | A/G | 0.00 | 0.00 | 0.11* | 0.50* | 8 | 115 | | |
| SNP 264 | C/T | 0.42 | 0.36 | 1.00* | 0.50* | 8 | 93 | 8 | 389 |
| SNP 5 | A/C | 0.33* | 0.50* | 1.00 | 1.00 | 9 | 56 | 9 | 238 |
| SNP 56 | C/G | 0.85* | 0.58* | 1.00 | 1.00 | 9 | 42 | 9 | 230 |
| SNP 271 | C/T | 0.00 | 0.00 | 0.11* | 0.50* | 9 | 98 | | |
| SNP 52 | A/T | 0.98 | 0.96 | 0.78* | 0.33* | 10 | 21 | 2 | 314 |
| SNP 187 | A/C | 0.38* | 0.67* | 1.00 | 1.00 | 10 | 74 | | |
| SNP 273 | C/T | 0.02 | 0.08 | 0.77* | 0.33* | 10 | 35 | | |

Xchange: Indicates the nucleotide exchange for the SNP marker;
Chr and cm_cons_map shows the chromosomal position on a consensus map of the SNP marker

10. Resistance to WCR of Maize Plants with Artificial Pathogen Infestation

The study was conducted at the University of Missouri (MU) Bradford Research and Extension Center, 9 km east of Columbia, Mo. USA through Bruce E. Hibbard (USDA-ARS, 205 Curtis Hall, University of Missouri, Columbia, Mo., USA) following an evaluation protocol similar to Hibbard et al. (2007) J. Plant Regist. 1: 151-152.

Three of the fields (Bradford4, Brookings, Rollins) selected for research had been planted with soybean in the previous year, therefore feral western corn root worms would not be found in the used plots. Eggs were suspended in dilute (0.15%) agar and application was calibrated so that approximately 1200 eggs per 30.5 cm went on either side of the infested plants. The agar was injected with a tractor implement specially made for this (Moellenbeck et al. (1994) J. Kans. Entomol. Soc. 67: 46-52). Two other fields (Bradford1 and Poultry) contained a natural infestation of the western corn rootworm that was augmented with 500 eggs per 30.5 cm. The Bradford farm and Poultry farm site has a Mexico silt loam soil type which was determined to be 2% sand, 70% silt, and 28% clay. The Rollins site has a Haymond loam which is 50% sand, 38.5% silt, 12.5% clay. Although the Brookings, S. Dak. site did not have soil test, the land is has been used for successful rootworm trials for many years.

Field trials were conducted on 5 different fields with 5 replications while the greenhouse trial had 2 different treatments (grass/no grass nurse crop) with 5 plot replications with each 2 sampling replications. The grass nurse crop was used to simulate weeds. Literature reports state that weeds are used by western corn rootworm larvae as food source for further development if main food source (maize roots) are not available or the maize variety is not a preferred feeding site. In total, 10 hybrids of different origin some with already known susceptibility (B37xH84) respectively resistance (MIR604) were tested. Event MIR604 is a genetically modified (GM) maize developed by Syngenta Seeds to confer field protection against the western corn root worm and the northern corn root worm. It also expresses a marker protein, PMI, that allows the plants to utilise mannose as a carbon source, acting as a selectable marker.

Larval sampling (Hibbard et al. (2004) J. Econ. Entomol. 97 (3):871-882) was timed for larval recovery at early $2^{nd}$ and early $3^{rd}$ instars. Whole root balls were gently placed in fine mesh polyethylene bags and hung over water pans in a greenhouse with the cooling turned off. Western corn rootworm larvae falling down into the water pans were stored in 95% ethanol until they could be processed. Separate plots were dug, washed, and rated for damage by using the Iowa scale 0-3 based on the number of pruned root nodes (Oleson et al. (2005) J. Econ. Entomol. 98:1-8). Root damage was scored on all 5 fields while larval recovery was evaluated only on fields Rollins, Bradford1 and Bradford2. Greenhouse larvae were extracted by using Tullgren funnels. Tullgren funnels create a temperature gradient of approximately 14° C. in a litter or soil sample, stimulating downward movement of soil arthropods into a collecting vessel.

TABLE 8

Mean root damage scores and larval recovery of replicated field trials with artificial infestation with western corn rootworm eggs 2008 on Bradford Research and Extension Center, MO, USA

| | | Means over all fields | |
|---|---|---|---|
| Pedigree | Origin | Root damage (0-3) | Larval Recovery (Number) |
| B37xH84 | Hibbard | 1.6 | 19.5 |
| MIR604 (GMO) | Syngenta | 0.1 | 8.6 |
| Isoline MIR604 (non-GMO) | Syngenta | 1.3 | 20.2 |
| SUM2068 | Südwestsaat GbR | 1.2 | 8.2 |
| SUM2162 | Südwestsaat GbR | 0.7 | 7.9 |
| CRW3(S1)C6 | Hibbard | 1.1 | 12.5 |
| NSS1xCRW3(S1)C6 | AgReliant Genetics | 0.9 | 10.3 |
| PI 583927 | Ames | 1.6 | 12.2 |
| CRW2(C5) | Hibbard | 1.0 | 12.2 |
| AR17056_16 | University of Illinois | 1.2 | 11.3 |
| Trial Mean | | 1.1 | 12.3 |

TABLE 9

Mean root damage (RD) and larval recovery (LR) numbers of different fields of replicated field trials with artificial infestation with western corn rootworm eggs 2008 on Bradford Research and Extension Center, MO, USA

| Pedigree | Poultry RD (0-3) | Brookings RD (0-3) | Rollins RD (0-3) | Rollins LR (Number) | Bradford4 RD (0-3) | Bradford4 LR (Number) | Bradford1 RD (0-3) | Bradford1 LR (Number) |
|---|---|---|---|---|---|---|---|---|
| B37xH84 | 2.1 | 2.6 | 1.1 | 15.4 | 0.4 | 13.1 | 1.6 | 30.0 |
| MIR604 | 0.1 | 0.1 | 0.0 | 0.5 | 0.0 | 0.3 | 0.2 | 25.0 |
| Isoline | 2.0 | 1.8 | 0.7 | 17.5 | 0.6 | 13.2 | 1.5 | 29.8 |
| SUM2068 | 1.8 | 1.5 | 0.8 | 3.3 | 0.3 | 1.5 | 1.4 | 19.9 |
| SUM2162 | 0.9 | 1.0 | 0.4 | 1.5 | 0.2 | 0.9 | 0.8 | 21.3 |
| CRW3(S1)C6 | 1.5 | 2.1 | 0.6 | 5.2 | 0.1 | 5.2 | 1.3 | 27.2 |
| NSS1xCRW3(S1)C6 | 1.5 | 1.6 | 0.5 | 4.5 | 0.1 | 7.7 | 0.9 | 18.6 |
| PI 583927 | 1.9 | 2.4 | 0.9 | 6.6 | 0.5 | 7.0 | 2.1 | 22.9 |
| CRW2(C5) | 1.6 | 2.1 | 0.4 | 3.7 | 0.3 | 5.4 | 0.8 | 27.6 |
| AR17056_16 | 1.6 | 2.1 | 0.6 | 6.8 | 0.5 | 6.1 | 1.0 | 20.9 |
| Location Mean | 1.5 | 1.7 | 0.6 | 6.5 | 0.3 | 6.1 | 1.1 | 24.3 |

TABLE 10

Mean larval recovery of 10 hybrids grown on greenhouse plots artificially infested with western corn rootworm eggs in a trial with two treatments (plots with/without grass as nurse crop)

| | without grass | | | with grass | | |
|---|---|---|---|---|---|---|
| Pedigree | Sample 1 | Sample 2 | Mean | Sample 1 | Sample 2 | Mean |
| B37xH84 | 9.3 | 7 | 8.2 | 7.7 | 6.2 | 7.0 |
| MIR604 | 0.2 | 0.9 | 0.6 | 1.5 | 1.6 | 1.6 |
| Isoline | 9.6 | 7.3 | 8.5 | 7.2 | 6 | 6.6 |
| SUM2068 | 2.6 | 3.3 | 3.0 | 3 | 1.6 | 2.3 |
| SUM2162 | 0.6 | 0.6 | 0.6 | 0.1 | 0.1 | 0.1 |
| CRW3(S1)C6 | 8.6 | 8.9 | 8.8 | 5.2 | 5 | 5.1 |
| NSS1xCRW3(S1)C6 | 3.4 | 4 | 3.7 | 3.9 | 5 | 4.5 |
| PI 583927 | 5.8 | 8.9 | 7.4 | 6.7 | 6.4 | 6.6 |
| CRW2(C5) | 4.9 | 5.6 | 5.3 | 6.9 | 6.5 | 6.7 |
| AR17056_16 | 6.4 | 6.3 | 6.4 | 6.4 | 5.7 | 6.1 |
| Sample Mean | 5.1 | 5.3 | 5.2 | 4.9 | 4.4 | 4.6 |
| Check grass plot without corn | | | | 4.1 | 4.1 | 4.1 |

Among all tested conventional hybrids with expected resistance against western corn rootworm SUM2162 showed the lowest root damage scores (Table 1 and Table 2). Only hybrid MIR604, conferring protection by a GMO trait, had a lower root damage rating. Larval recovery of SUM2068 and SUM2162 was comparable to the larval recovery observed on plots with the GMO hybrid MIR604. Compared to the most susceptible hybrid of the trial, non-GMO version (isoline) of MIR604, SUM2068 showed a 59.4% lower larval recovery and even more reduction was observed for SUM2162 with 60.9%. In comparison to the other as resistant classified hybrids (CRW3(S1)C6, NSS1× CRW3(S1)C6, PI583927, CRW2(C5), AR17056_16) SUM2068 and SUM2162 were superior in larval recovery (SUM2068: 20.4% and SUM2162: 23.3% lower larval recovery compared to the best other resistant hybrid NSS1× CRW3(S1)C6).

Larval recovery numbers were consistent in field and greenhouse experiments. Also in these trials hybrids SUM2068 and SUM2162 showed the lowest larval recovery numbers compared to all tested conventional hybrids (Table 3). In the greenhouse experiment SUM2162 showed the same low larval recovery number as MIR604 in the "without grass" nurse crop treatment

DESCRIPTION OF THE FIGURES

FIG. 3 Infestation of hybrid plants with WCR. The hybrids were subjected to a so-called strip test, i.e. they were cultivated on a field (strip) that was WCR contaminated. Net tents were arranged over a part of this field, and the infestation was quantified by counting the number of WCR beetles which were attracted by a pheromone trap under the tents.

REFERENCES

Figure 1:
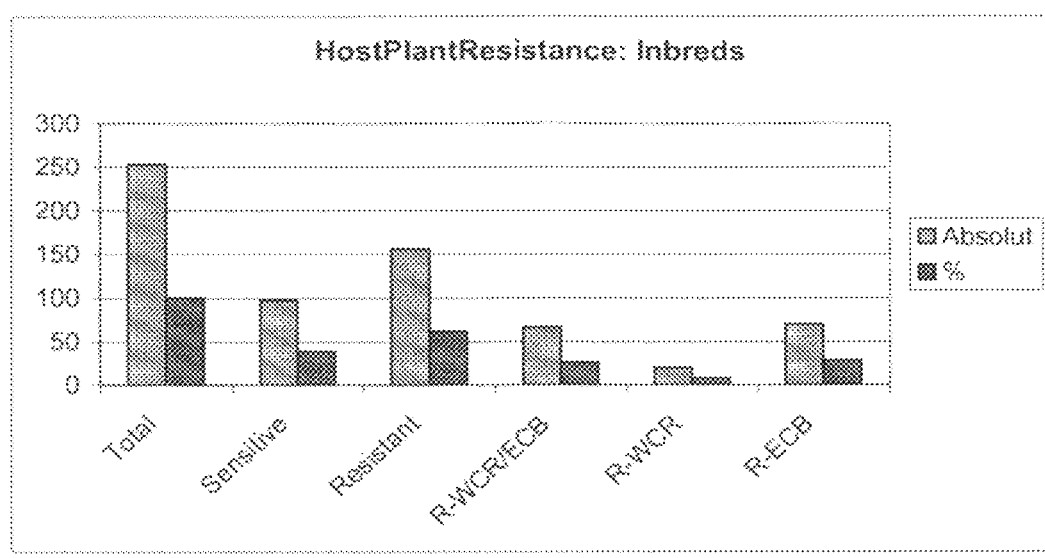
FIG. 1 Results from inbred lines that have been tested for resistance against WCR and/or ECB. The inbred lines were sowed in a randomized block arrangement in two rows of a length of 5 meters. The experiment was reproduced. The absolute number of plants and the percentage of plants which are "lodged" (i.e. the plants that are susceptible to WCR and ECB) is represented on the Y-axis. The evaluation is based on a lodging rating scale from 1 (resistant) to 9 (susceptible or sensitive). The graph shows the total number of plants, the number of susceptible (sensitive) plants and the total number of resistant plants, as well as the percentage of the respective plant population in relation to the total number of plants. The resistant plants are further subdivided into plants being resistant against both WCR and ECB and plants being resistant against only WCR or EBC.
Figure 2:
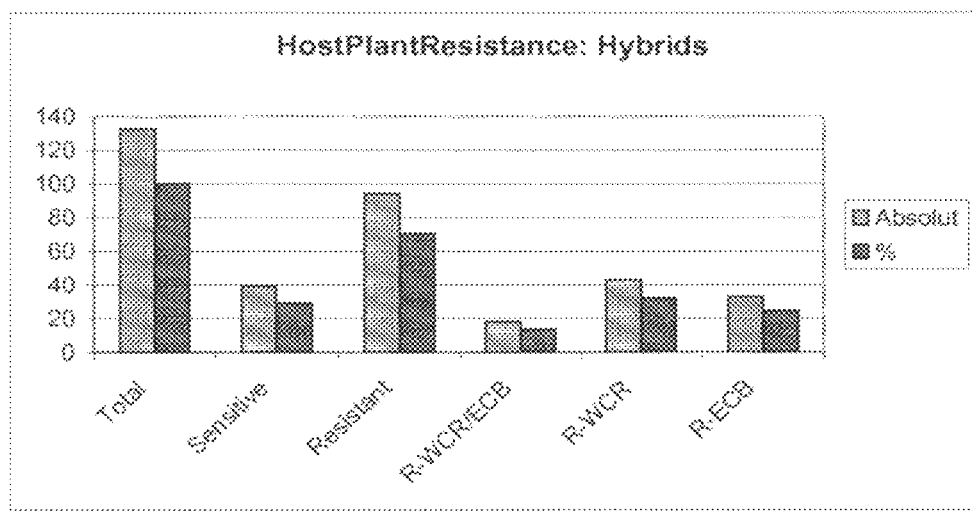
FIG. 2 The same representation as FIG. 1, but with hybrid plants.
Figure 3A:
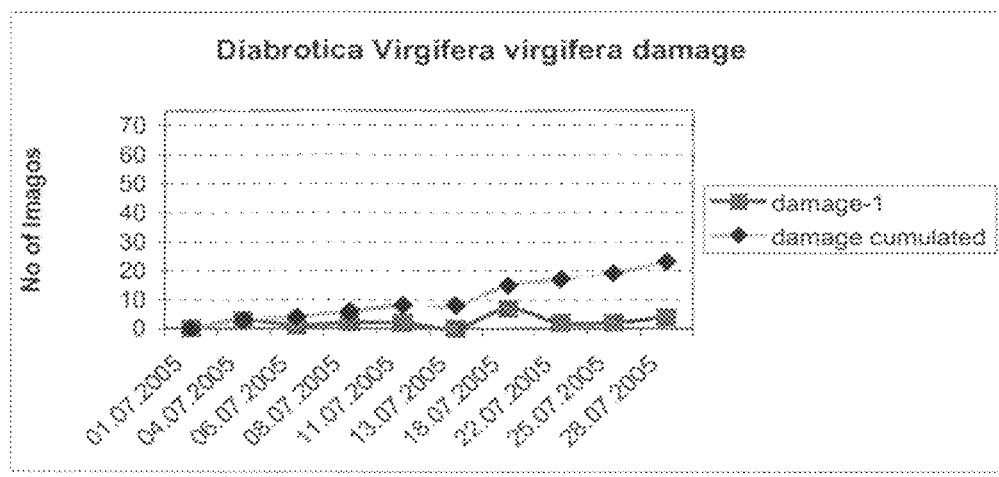
FIG. 3a shows the infestation at the HSB location where a relatively low WCR infestation compared to other locations occurs.
Figure 3B:
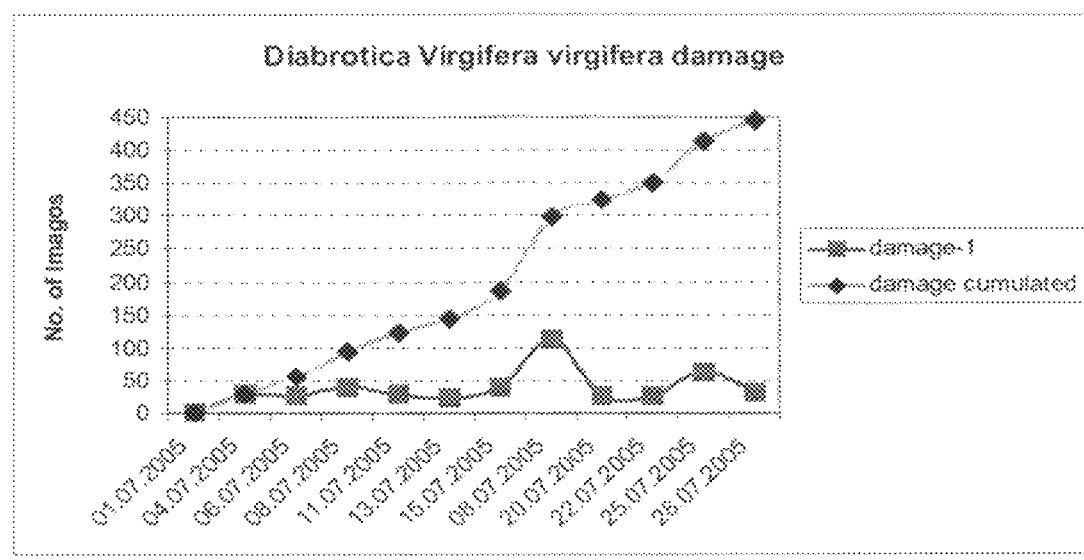
FIG. 3b shows the infestation at the HBB location, where a relatively high infestation pressure of WCR is present. The lower line shows the number of counted beetles at individual time points, and the upper line shows the cumulated infestation over the whole time period.
Figure 4:
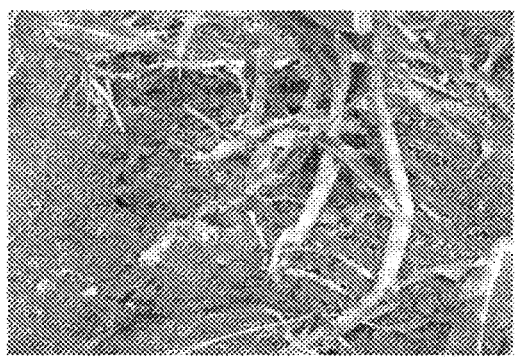
FIG. 4 Photographic representation of susceptible (left photograph) and resistant (right photograph) hybrids, wherein the susceptible hybrids "lodged" as a result of root damage, while the resistant hybrids stay in an upright position.
Figure 4:
Figure 5:
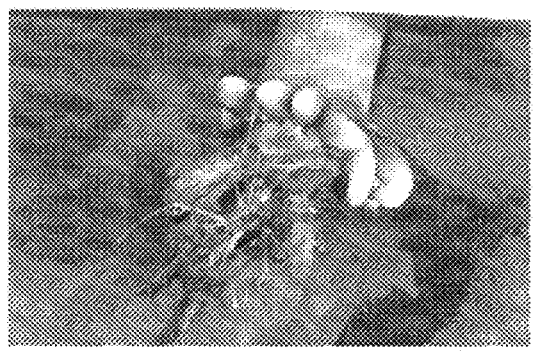
FIG. 5 Photographic representation of root damage, wherein the susceptible hybrid (left photograph) shows strongly stunted roots, while the resistant hybrid (right photograph) shows normal root growth.
Figure 5:
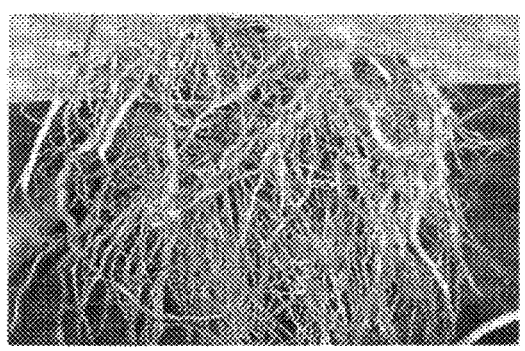
Figure 6:
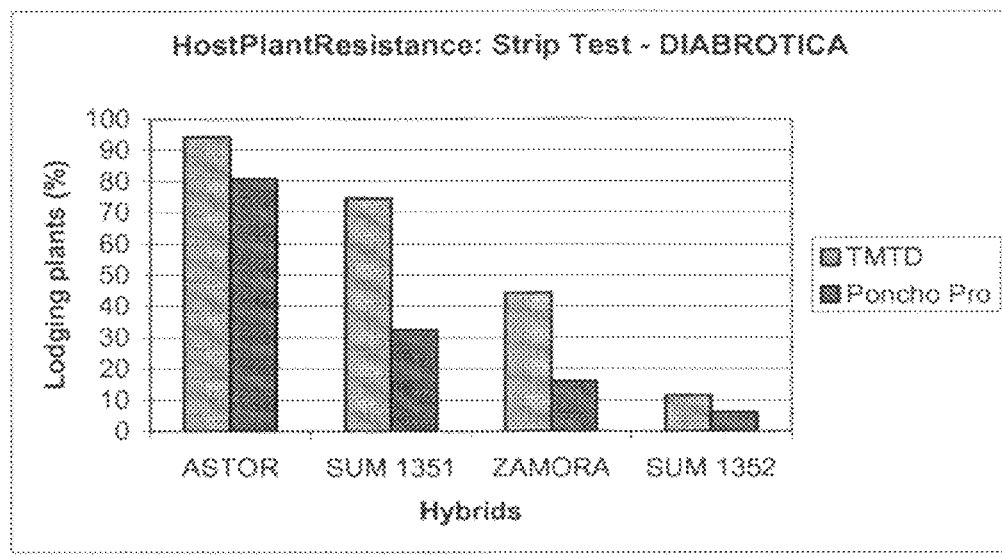
FIG. 6 Results of WCR damage on different hybrids (Astor, Sum 1351, Zamora, Sum 1352). The hybrids were treated with the fungicide TMTD (tetramethylthiuram disulfide, 30 g TMTD/50000 maize grains) either alone or in addition with the insecticide substance clothianidin (PonchoPro®, 63 g/50000 maize grains). The percentage of plants which "lodged" as a result of WCR damage is represented. The evaluation is based on the lodging rating scale. "Astor" is a very susceptible hybrid plant. "Zamora" is a hybrid that shows under certain conditions tolerance to WCR due to a very good root system. The hybrid Sum 1351 derives from only one resistant parental plant (R 7240×AJ 1494), while hybrid Sum 1352 derives from two parental plants which are both resistant (R 7222×AJ 1499).
Figure 7:
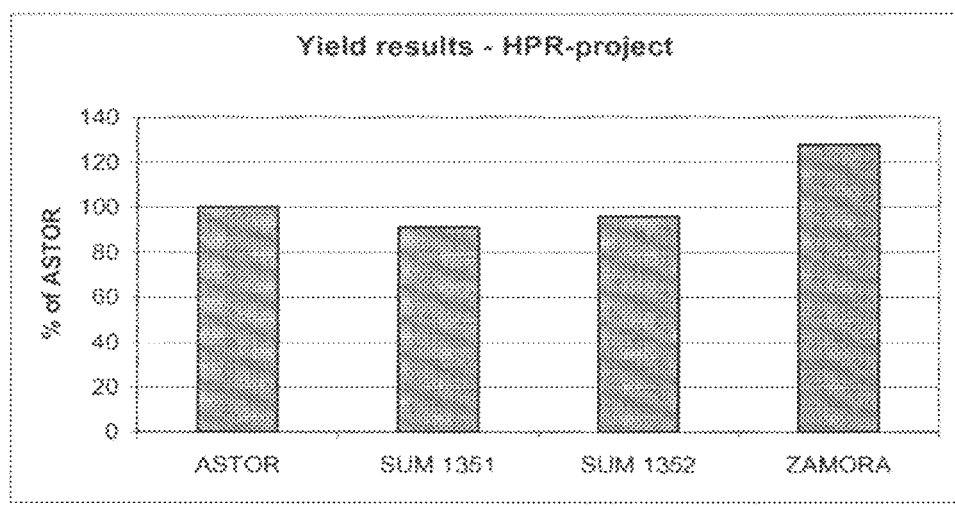
FIG. 7 Yield results (strip test). The experiments were repeated four times on a parcel of land that was composed of four rows, each one measuring 25 meters. The hybrids Astor and Zamora show better yields than the hybrids SUM 1351 and SUM 1352 because the latter are not yet elite material.
Figure 8:
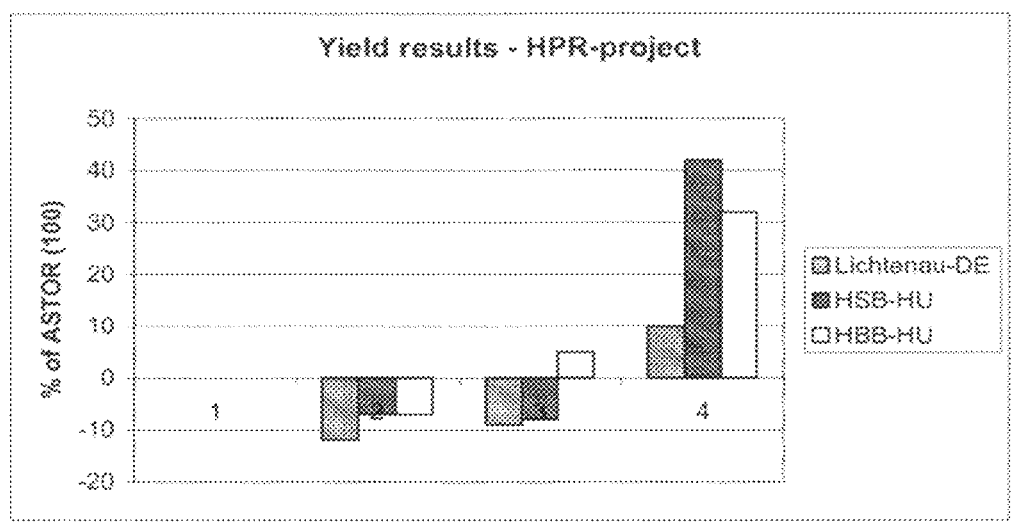
FIG. 8 Yield results on different locations (strip test). The German location Lichtenau shows only slight ECB infestation, while the Hungarian location HBB shows a high infestation pressure of WCR. The location HSB is considered to show medium infestation of WCR. The SUM 1352 hybrid shows better yield results than the very susceptible hybrid Astor in a location of high WCR infestation.
Figure 9A:
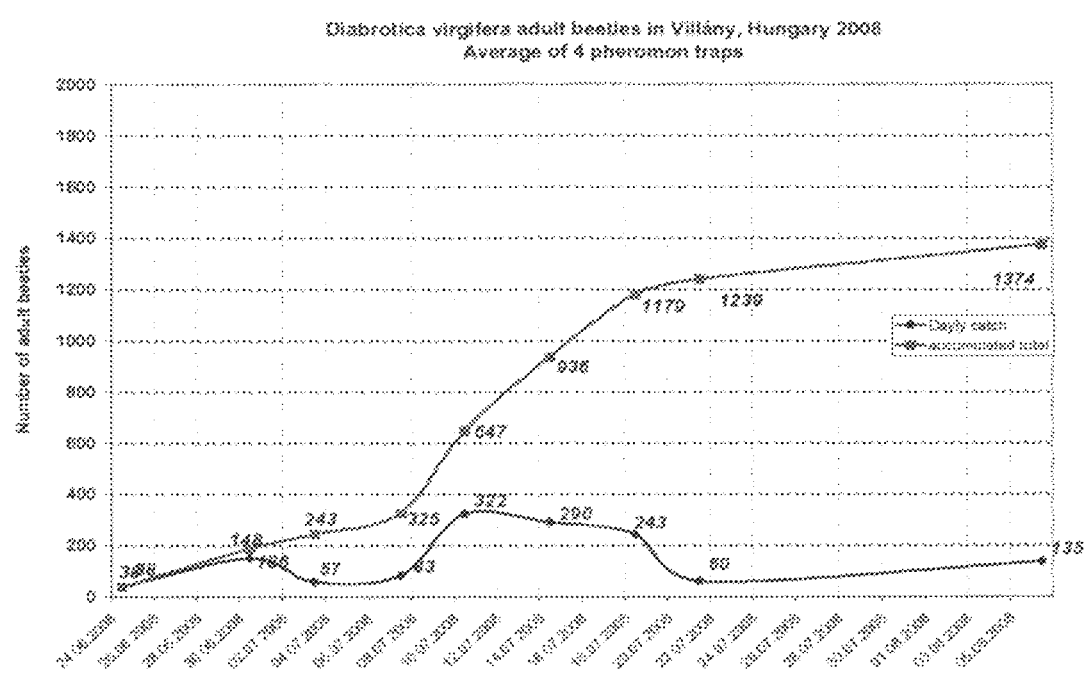
FIG. 9 Average number of caught WCR beetles from four pheromone traps on locations Villany (a), Dalmand (b) and Szentlörinc (c) in Hungary 2008.
Figure 9B:
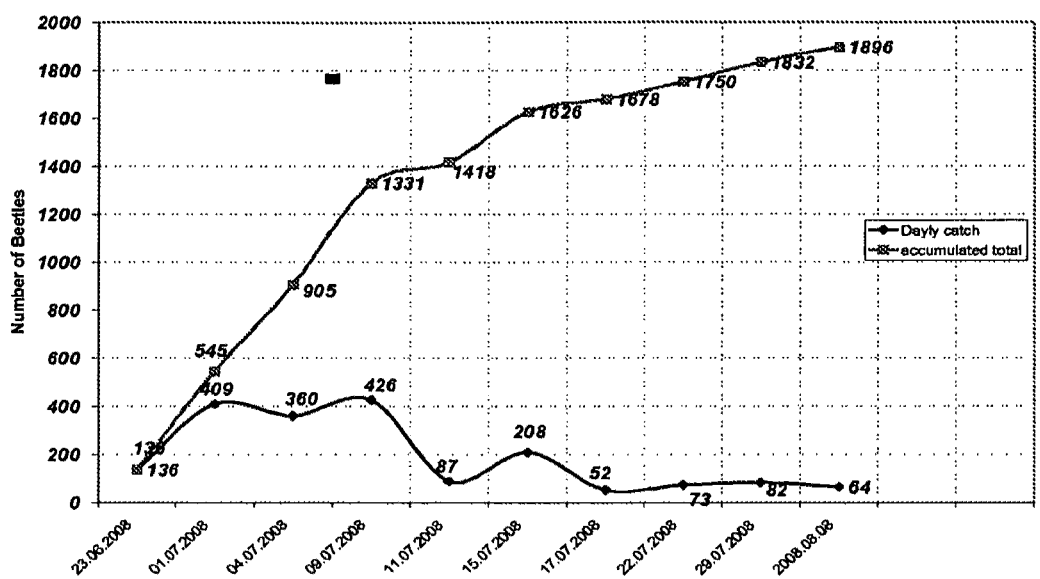
Figure 9C:
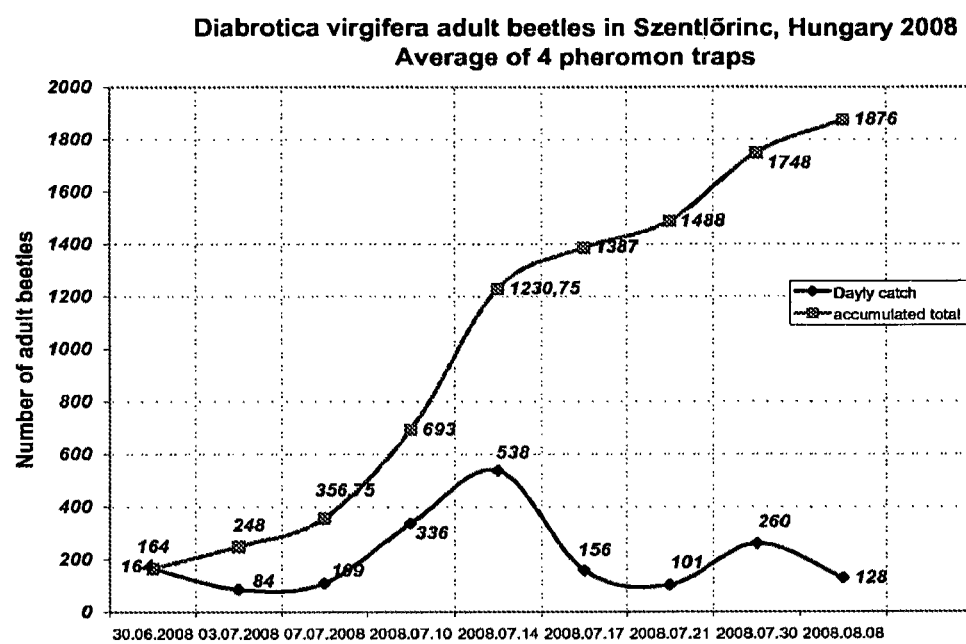
Figure 10A:
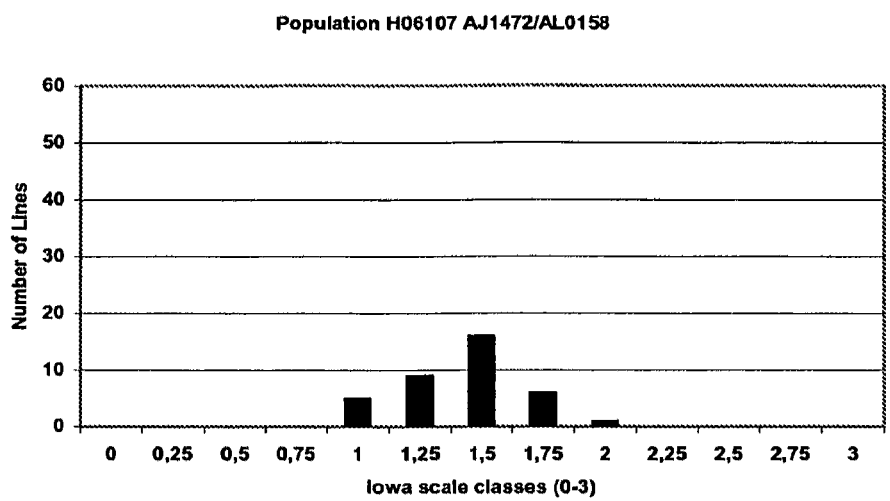
FIG. 10 Distribution of single lines of populations H06107 (a) and H06103 (b) for WCR resistance. Root damage was evaluated with the new Iowa scale from 0-3. Presented are means of locations Dalmand and Villany.
Figure 10B:
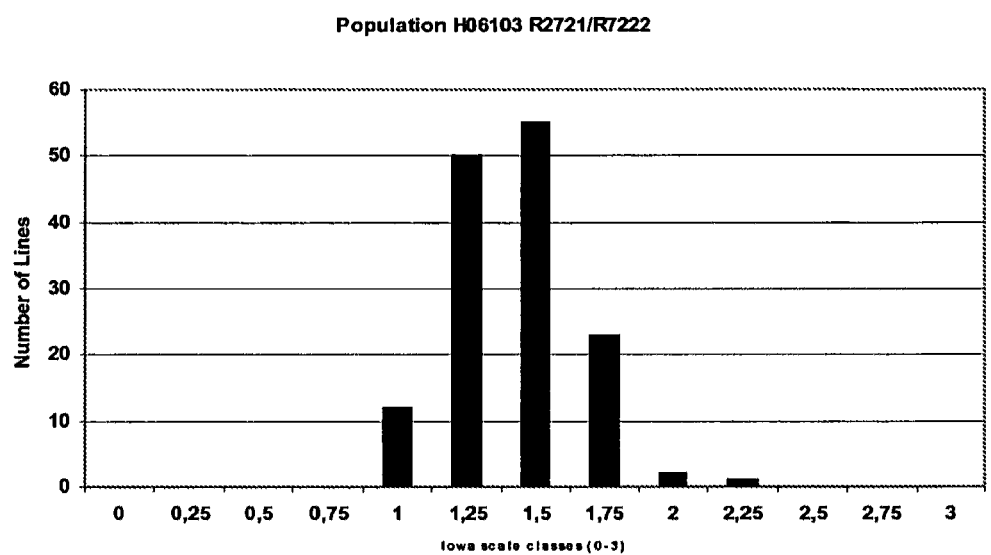

Bohn, M., Groh, S., Khairallah, M. M., Hoisington, D. A., Utz, H. F. and Melchinger, A. E. (2001) Re-evaluation of the prospects of marker-assisted selection for improving insect resistance against *Diatraea* spp. in tropical maize by cross validation and independent validation. *Theor. Appl. Genet.*, 103: 1059-1067

Capinera, J. L., Epsky, N. D., and Thompson, D. C. (1986) Effects of adult western corn rootworm (Coleoptera: *Chrysomelidae*) ear feeding on irrigated field corn in Colorado. *Journal of Economic Entomology*, 79: 1609-1612.

EPPO (1996) Situation of *Diabrotica virgifera* in Serbia (YU). From International Workshop "Western Corn Rootworm in Europe 95", Gödöllö (HU), 1995-11-08. EPPO Resporting Service (1996/006).

EPPO (1998) *Diabrotica virgifera* trapped near Venezia airport (Italy) From: Osservatorio per le Malattie delle Piante di Verona, Servizio Fitosanitario Regionale del Veneto, 1998-08. EPPO Reporting Service (1998, 98/161).

Fengming Y, L I Songgang, X U Chongren, L I N Changshan 1996: Antifeedant Property of DIMBOA and Its Effect on Growth and Development of the Asian Corn Borer, *Ostrinia furnacalis* (GUENEE), P. D. 1996-03-20 Vol. 32 No. 2 pp. 254-260; www.pku.edu.cn/academic/xb/96/y96218.html Flint-Garcia S A, Thornsberry J M, Buckler E S (2003) Structure of linkage disequilibrium in plants. Annu Rev Plant Biol 54: 357-374

Gavloski, J. E., Whitfield, G. H. & Ellis, C. R. (1992) Effect of larvae of western corn rootworm and of mechanical root pruning on sap flow and growth of corn. *Journal of Economic Entomology*, 85: 1434-1441.

Gianessi, L., Sankula, S., and Reigner, N. 2003. Plant biotechnology: Potential impact for improving pest management in European agriculture. Maize Case Study. The National Center for Food and Agricultural Policy, Washington.

Hansen L. M., Role of DIMBOA in the partial resistance of winter wheat to the grain aphid (*Sitobion avenae* F.); Second European Allelopathy Symposium, June 2004, Pulawy, Poland Jarvis, J. L., Clark, R. L., Guthrie, W. D., Berry, E. C., Russell, W. A. 1984. The relationship between second-generation European corn borers and stalk rot fungi in maize hybrids. Maydica 24: 247-263.

Jennings, C. W., Russell, W. A., and Guthrie, W. D. (1974) Genetics of Resistance in Maize to First and Second-Brood European Corn Borer. *Crop Science* 14: 394-398

Krysan, J. L. & Miller, T. A. (1986) Methods for the study of *Diabrotica*. Springer Verlag, New York, 260 pp.

Langenbruch, G. A., and Szewczyk, D. 1995. Maisziinsler (*Ostrinia nubialis*) an Mais im Süden Nordrhein-Westfalens. Nachrichtenblatt Deutscher Pflanzenschutzdienst. 47: 326.

Levine, E. & Oloumi-Sadeghi, H. (1991) Management of Diabroticite rootworms in corn. *Annual review of Entomology*, 36: 229-255.

Lew, H., Adler, A., Edinger E. 1991. Moniliform and the European corn borer (*Ostrinia nubialis*). Mycotox. Res. 7A:71-76.

Magg, T. 2004. Resistance of maize (*Zea mays* L.) against the European corn borer (*Ostrinia nubialis* Hb.) and its association with mycotoxins produced by *Fusarium* spp. Dissertation an der Universität Hohenheim.

Meloche, F., Filion, P., Tremblay, G. & LeSage, L. (2001) [Advance of *Diabrotica virgifera virgifera* (Coleoptera: Chrysomelidae) in corn fields in Quebec and sampling in soybean plants in Ottawa, Ontario] *Phytoprotection*, 82: 35-38.

Metcalf, R. L. (1976) Organochlorine insecticides, survey, and prospects. In: Metcalf, R. L. & McKelvey, J. J. (Eds.) *The future for insecticides. Needs and prospects. Proceedings of a Rockefeller Foundation Conference Bellagio, Italy*, Apr. 22-27, 1974. John Wiley, London. pp. 223-285.

Metcalf, R. L. & Metcalf, R. A. (1993) *Destructive & Useful Insects*, 5th Edn., McGraw-Hill, New York Michelmore R W, Paran I, Kesseli R V (1991) Identification of markers linked to disease-resistance genes by bulked segregant analysis: A rapid method to detect markers in specific genomic regions by using segregating populations. Proc Natl Acad Sci USA 88: 9828-9832

Niemeyer, H. M. & Perez, F. J. Potential of hydroxamic acids in the control of cereal pests, diseases, and weeds. 1995, Pp. 250-270. In Inderjit Dakshini, K. M. M. & Einhellig, F. A. (Eds.). Allelopathy organisms, processes, and applications. ACS symposium series. American Chemical Society, Washington D.C.

Oleson, J. D., Park, Y., Nowatzki, T. M., Tollefson, J. J. 2005. Node injury scale. J. Econ Entomol. 98(1): 1-8).

Onstad, D. W., Crowder, D. W., Isard, S. A., Levine, E., Spencer, J. L., O'Neal, M. E., Tarcliffe, S. T., Gray, M. E., Bledsoe, L. W., Di Fonzo, C. D., Eisley, J. B. and Edwards, C. R. (2003) Does landscape diversity slow the spread of rotation-resistant Western corn rootworm (Coleoptera: *Chrysomelidae*)? *Environmental Entomology*, 32 (5), 992-1001.

Pritchard, J. K., Stephens, M., and Donnelly, P. 2000. Inference of population structure using multilocus genotype data. Genetics 155: 945-959

Roush, R. 2006. Managing virulence to Bt insecticidial crops: Think of Bt as a plant resistance gene, not as an insectizide. Seventeenth Biennial International Plant Resistance to insects workshop. Apr. 9$^{th}$-12$^{th}$ 2006, Purdue Memorial Union, purdue University, West Lafayette, Ind., USA.

Scheurer K S, Friedt W, Huth W, Waugh R, Ordon F (2001) QTL analysis of tolerance to a German strain of BYDV-PAV in barley (*Hordeum vulgare* L.). Thero Appl Genet. 103:1074-1083

Schulz, B., Kreps R., Klein, D., Gumber, R. K. and Melchinger, A. E. 1997. Genetic variation among European maize inbreds for resistance to the European corn borer and relations to agronomic traits. Plant Breeding 116: 415-422.

Werner K, Pellio B, Ordon F, Friedt W (2000a) Development of an STS marker and SSRs suitable for marker-assisted selection for the BaMMV resistance gene rym9 in barley. Plant Breeding 119: 517-519

Wrigh R t, J. Witkowski 1997. The European Corn Borer: Biology & Management, University of Nebraska-Lincoln. South Central Research & Extension Center

The invention claimed is:

1. *Zea mays* plant which is inbred and is resistant to both Western Corn Root Worm and European Corn Borer, wherein the plant does not comprise a gene expression cassette expressing a protein derived from *Bacillus thuringiensis*, and is at least 20% more resistant to Western Corn Root Worm and European Corn Borer as compared to *Zea mays* line NGSDRW 1 (SC2)C4-15-252, wherein the resistance is determined by use of a scale selected from the group of a 1-9 lodging rating scale and a 0-3 Iowa scale and compared to non-resistant control plants grown in the same environmental conditions, wherein the resistance to Western Corn Root Worm and European Corn Borer is detected by at least two single nucleotide polymorphisms (SNPs), and wherein the first SNP is an A/T nucleotide exchange located at position 197 cM_IBM_map on chromosome 5, and the second SNP is an A/C nucleotide exchange located at position 383 cM_IBM_map on chromosome 2.

2. *Zea mays* plant according to claim 1, wherein the resistance is determined by use of the 1-9 lodging rating scale, and compared to non-resistant control plants grown in the same environmental conditions.

3. *Zea mays* plant according to claim 1, wherein the resistance to Western Corn Root Worm is determined by use of the 0-3 Iowa scale, and compared to non-resistant control plants grown in the same environmental conditions.

4. *Zea mays* plant according to claim 3, wherein the Iowa root score is between 0.2 and 1.2.

5. *Zea mays* plant according to claim 1 wherein the plant further does not express an insecticidal protein derived from a bacterium, wherein the bacterium is a bacterium other than *Bacillus thuringiensis*.

6. *Zea mays* plant according to claim 5 wherein the plant further does not express a transgenic insecticidal protein.

7. *Zea mays* plant according to claim 5 wherein the plant further does not express a transgenic pesticidal protein.

8. *Zea mays* plant according to claim 5 wherein the plant is at least two times less susceptible to Western Corn Rootworm compared to the reference *Zea mays* plant R 1437.

9. *Zea mays* plant according to claim 5 wherein the plant is at least two times less susceptible to European Corn Borer compared to the reference *Zea mays* plant R 6080.

10. *Zea mays* plant according to claim 5 wherein the susceptibility is determined by the number of larvae of the roots, and compared to non-resistant control plants grown in the same environmental conditions.

11. *Zea mays* plant according to claim 5 wherein the plant is resistant to the Fall Armyworm and/or to the Black Cutworm.

12. Method for producing a *Zea mays* plant which is resistant to both Western Corn Root Worm and European Corn Borer, comprising the steps of:

a) detecting at least two single nucleotide polymorphisms (SNPs), wherein the first SNP is an A/T nucleotide exchange located at position 197 cM_IBM_map on chromosome 5, and the second SNP is an A/C nucleotide exchange located at position 383 cM_IBM_map on chromosome 2, in genetic material isolated from a *Zea mays* plant,
b) identifying plants having the at least two SNPs,
c) crossing an identified *Zea mays* plant of b) with a second *Zea mays* plant not having the at least two SNPs,
d) collecting seed from the cross in step c); and
e) growing a progeny *Zea mays* plant from said seed which comprises said at least two SNPs, thereby producing a *Zea mays* plant which is resistant to both Western Corn Root Worm and European Corn Borer.

13. Method according to claim 12, further comprising the step of confirming resistance to Western Corn Root Worm of the plants having at least one single nucleotide polymorphism, wherein the step of confirming resistance to Western Corn Root Worm is performed using a method selected from the group consisting of determining the lodging on a 1-9 lodging rating scale and determining root damage by use of the 0-3 Iowa scale or determining larval recovery; compared to non-resistant control plants grown in the same environmental conditions.

* * * * *

UNITED STATES PATENT AND TRADEMARK OFFICE
CERTIFICATE OF CORRECTION

PATENT NO.        : 9,603,321 B2
APPLICATION NO.   : 12/674162
DATED             : March 28, 2017
INVENTOR(S)       : Peter Goertz and John A. Mihm It is certified that error appears in the above-identified patent and that said Letters Patent is hereby corrected as shown below:

In the Claims

Claim 7, Column 34, Line 45, please delete "claim 5" and insert -- claim 6 -- therefor.

Claim 8, Column 34, Line 47, please delete "claim 5" and insert -- claim 7 -- therefor.

Claim 9, Column 34, Line 51, please delete "claim 5" and insert -- claim 8 -- therefor.

Claim 10, Column 34, Line 54, please delete "claim 5" and insert -- claim 8 -- therefor.

Claim 11, Column 34, Line 58, please delete "claim 5" and insert -- claim 10 -- therefor.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*